United States Patent
Soucy et al.

(10) Patent No.: US 11,406,737 B2
(45) Date of Patent: Aug. 9, 2022

(54) GELATIN/ELASTIN COMPOSITES FOR PERIPHERAL NERVE REPAIR

(71) Applicant: Northeastern University, Boston, MA (US)

(72) Inventors: Jonathan R. Soucy, Boston, MA (US); Ehsan Shirzaei Sani, Boston, MA (US); Abigail N. Koppes, Charlestown, MA (US); Ryan A. Koppes, Charlestown, MA (US); Nasim Annabi, Cambridge, MA (US)

(73) Assignee: Northeastern University, Boston, MA (US)

( * ) Notice: Subject to any disclaimer, the term of this patent is extended or adjusted under 35 U.S.C. 154(b) by 765 days.

(21) Appl. No.: 16/109,455

(22) Filed: Aug. 22, 2018

(65) Prior Publication Data

US 2019/0070338 A1 Mar. 7, 2019

Related U.S. Application Data

(60) Provisional application No. 62/548,899, filed on Aug. 22, 2017.

(51) Int. Cl.
| | |
|---|---|
| *A61L 27/52* | (2006.01) |
| *A61L 27/38* | (2006.01) |
| *A61L 27/26* | (2006.01) |
| *A61L 27/22* | (2006.01) |
| *A61B 17/11* | (2006.01) |
| *A61B 17/00* | (2006.01) |

(52) U.S. Cl.
CPC .......... *A61L 27/52* (2013.01); *A61B 17/1128* (2013.01); *A61L 27/222* (2013.01); *A61L 27/227* (2013.01); *A61L 27/26* (2013.01); *A61L 27/383* (2013.01); *A61L 27/3878* (2013.01); *A61B 17/00491* (2013.01); *A61B 2017/1132* (2013.01); *A61L 2430/32* (2013.01)

(58) Field of Classification Search
None
See application file for complete search history.

(56) References Cited

FOREIGN PATENT DOCUMENTS

WO WO 2016/022807 * 2/2016 ............. A61L 24/04

OTHER PUBLICATIONS

Annabi etal, Biomaterials, 2017, vol. 2139: 229-243. (Year: 2017).*
Annabi et al. "Engineered cell-laden human protein-based elastomer", *Biomaterials* 2013, 34, 5496-5505.
Annabi, N., et al. "Highly Elastic and Conductive Human-Based Protein Hybrid Hydrogels", *Adv. Mater.* 2016, 28, 40-49.
Annabi, N., et al., "Engineering a highly elastic human protein-based sealant for surgical applications", *Sci. Transl. Med.* 9, eaai7466 (2017), 14 pages.
Chen, Y.C., et al., "Functional Human Vascular Network Generated in Phtocrosslinkable Gelatine Methacrylate Hydrogels", *Adv. Fund. Mater.* 2012, 22, 2027-2039.
Chuang, T.H., et al. "A Novel Internal Fixator Device for Peripheral Nerve Regeneration", *Tissue Eng Part C Methods* 2013, 19, 427-437.
Kehoe, S., et al. "FDA approved guidance conduits and wraps for peripheral nerve injury: A review of materials and efficacy", *Injury* 2012, 43, 553-572.
Khaing, Z. A., et al. Injectable Hydrogels for Spinal Cord Repair: A Focus on Swelling and Intraspinal Pressure, *Cells Tissues Organs* 2016, 202, 67, 34 pages.
Koppes, A. N. et al. "Electrical Stimulation of Schwann Cells Promotes Sustained Increases in Neurite Outgrowth", *Tissue Eng Part A* 2014, 20, Nos. 3 and 4, , 494-506.
Koppes, A. N. et al. "Robust neurite extension following exogenous electrical stimulation within single walled carbon nanotube-composite hydrogels", *Acta Biomater* 2016, 39, 34-43.
Lam, J., et al. A factorial analysis of the combined effects of hydrogel fabrication parameters on the in vitro swelling and degradation of oligo(poly(ethylene glycol) fumarate) hydrogels, *J Biomed Mater Res A* 2014, 102, 3477-3487.
Lang, N, et al. ., "A blood-resistant surgical glue for minimally invasive repair of vessels and heart defects",. Sci Transl Med 2014;6:218ra6, 6(218): 1-12.
Liu, H., et al. "Matrix Metalloproteinase Inhibition Enhances the Rate of Nerve Regeneration in Vivo by Promoting Dedifferentiation and Mitosis of Supporting Schwann Cells", *J Neuropalhol Exp Neurol* 2010, 69(4), 386-395.
Liu, Z., el al. "Specific Marker Expression and Cell State of Schwann Cells during Culture In Vivo", *PLoS One* 2015, 10, e0123278, 17 pages. Mehdizadeh, M., et al., "Design Strategies and Applications of Tissue Bioadhesives", *Macromol Biosci* 2013, 13, 271-288.

(Continued)

*Primary Examiner* — Allison M Fox
(74) *Attorney, Agent, or Firm* — Hamilton, Brook, Smith & Reynolds, P.C.

(57) ABSTRACT

Neurosupportive materials that possess strong tissue adhesion were synthesized by photocrosslinking two polymers, gelatin methacryloyl (GelMA) and methacryloyl-substituted tropoelastin (MeTro). The engineered materials exhibited tunable mechanical properties by varying the GelMA/MeTro ratio. In addition, GelMA/MeTro hydrogels exhibited 15-fold higher adhesive strength to nerve tissue ex vivo compared to traditionally used fibrin-based materials. Furthermore, the composites were shown to support Schwann cell (SC) viability and proliferation, as well as neurite extension and glial cell participation in vitro, which are essential cellular components for nerve regeneration. Finally, subcutaneously implanted GelMA/MeTro hydrogels exhibited slower degradation in vivo compared with pure GelMA, indicating its potential to support the growth of slowly regenerating nerves. Thus, GelMA/MeTro composites may be used as clinically relevant biomaterials to regenerate nerves and reduce the need for microsurgical suturing during nerve reconstruction.

18 Claims, 22 Drawing Sheets
(11 of 22 Drawing Sheet(s) Filed in Color)

(56) References Cited

OTHER PUBLICATIONS

Nectow, A.R., et al. "Biomaterials for the Development of Peripheral Nerve Guidance Conduits", *Tissue Eng Part B Rev* 2012, 18, 40-50.
Nichol, J.W., et al. "Cell-laden microengineered gelatin methacrylate hydrogels", *Biomaterials* 2010, 31, 5536-5544.
Park, S., et al., "Optogenetic control of nerve growth", *Sci Rep* 2015, 5, 9669, 9 pages.
Rickett, T., et al. "A Photo-Crosslinkable Chitosan Hydrogel for Peripheral Nerve Anastomosis", *Int Conf Biomed* 2009, DOI: 10.1109/BMEI.2009.53054601078, 5 pages.
Smart, J.D. , "The basics and underlying mechanisms of mucuadhesion", *Adv Drug Deliv Rev* 2005, 57, 1556-1568.
Vandooren, J., et al. "Biochemistry and molecular biology of gelatinase B or matrix metalloproteinase-9 (MMP-9); The next decade", *Crit Rev Biochem Mol Biol* 2013, 48, 222-272.
Wolford, L.M., et al. "Considerations in Nerve Repair", *Proc (Bayl Univ Med Cent)* 2003, 16, 152-56.
Yao, Mr., et al. "Phototoxicity is Not Associated with Photochemical Tissue Bonding of Skin", *Lasers Surg Med* 2010, 42, 123-131.
Yidong, T., et al., "Transient tropoelastin nanoparticles are early-stage intermediates in the coacervation of human tropoelastin whose aggregation is facilitated by heparan sulfate and heparin decasaccharides", Matrix Biology 2010; 29:152-159.

* cited by examiner

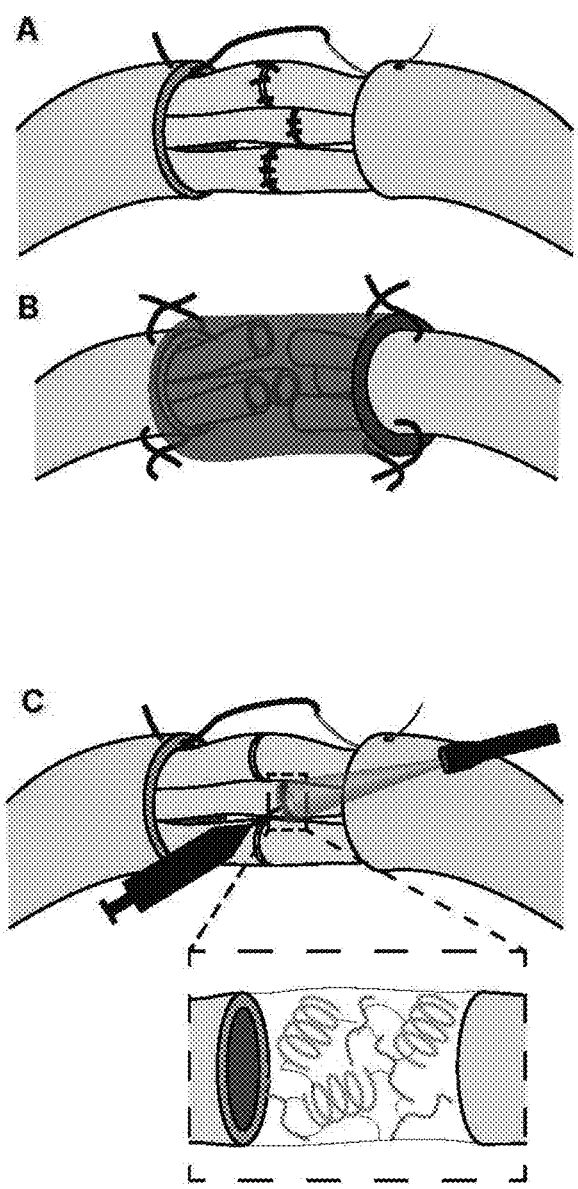
FIG. 1A-C

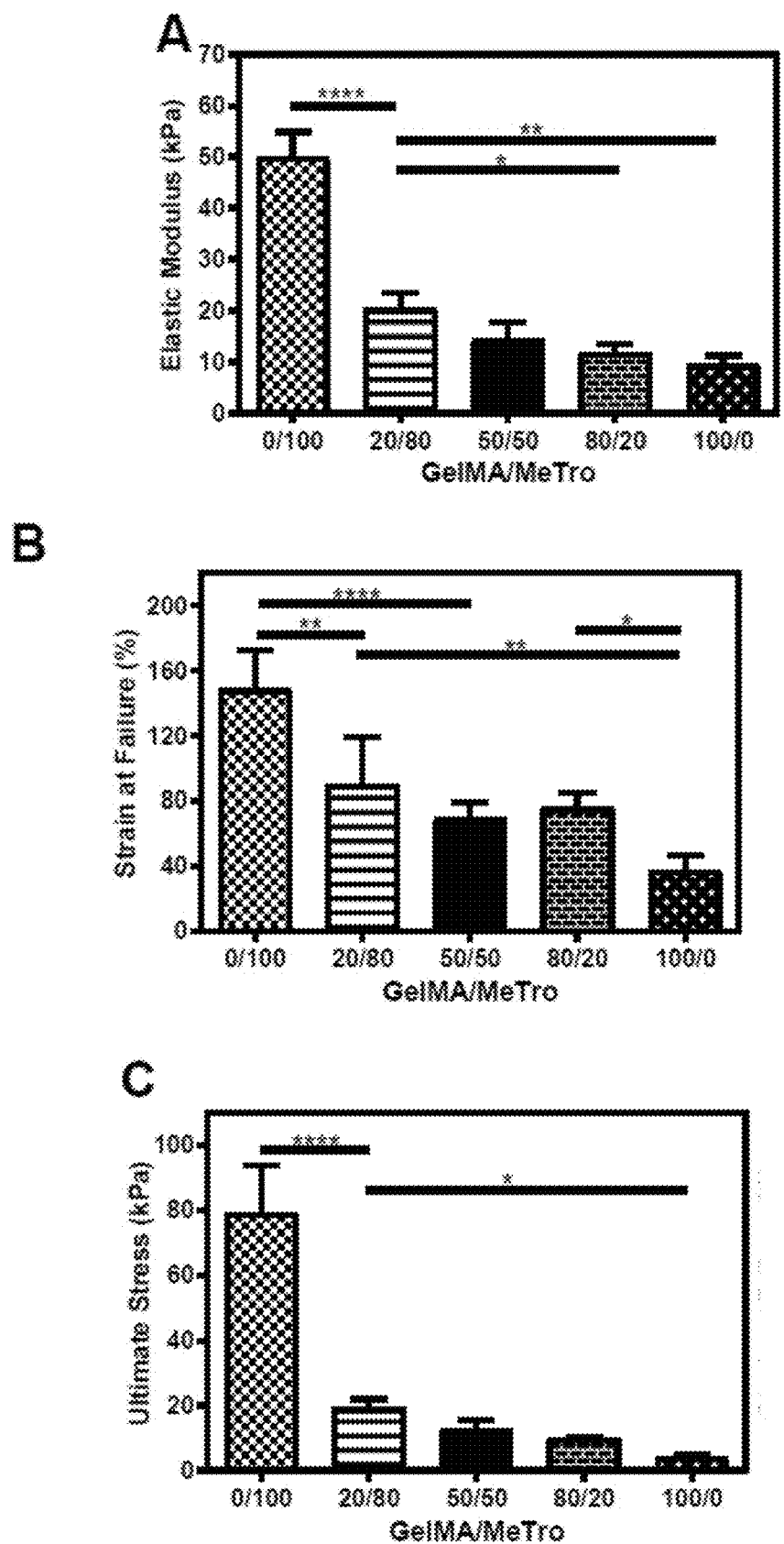
FIG. 2A-C

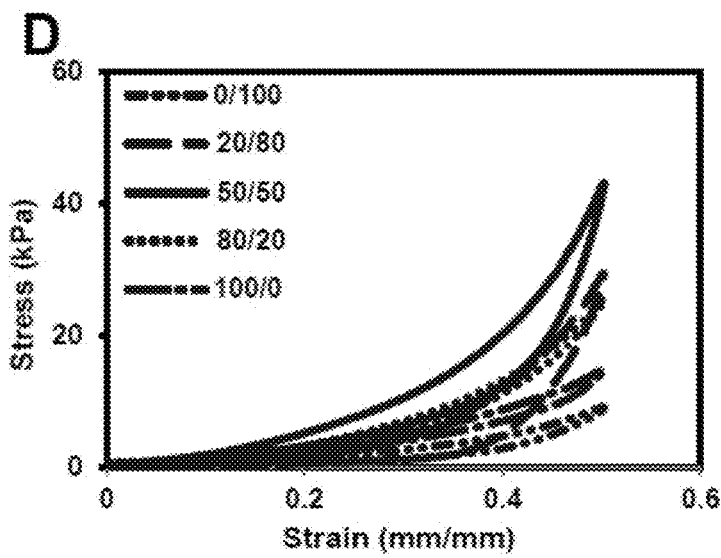
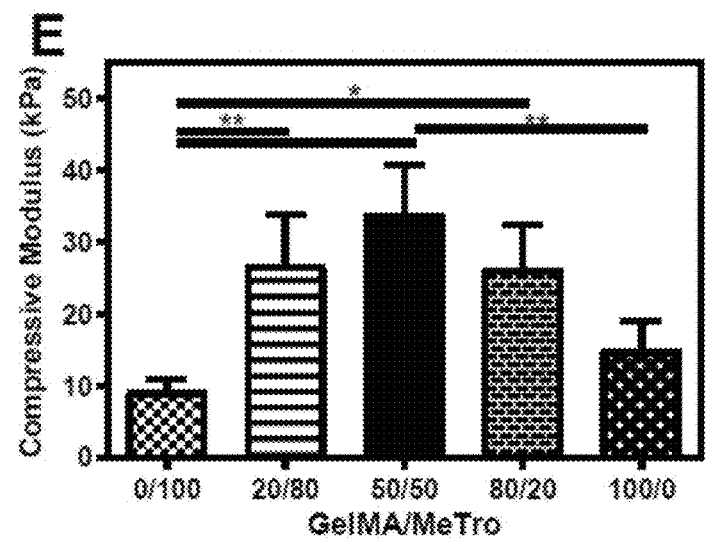
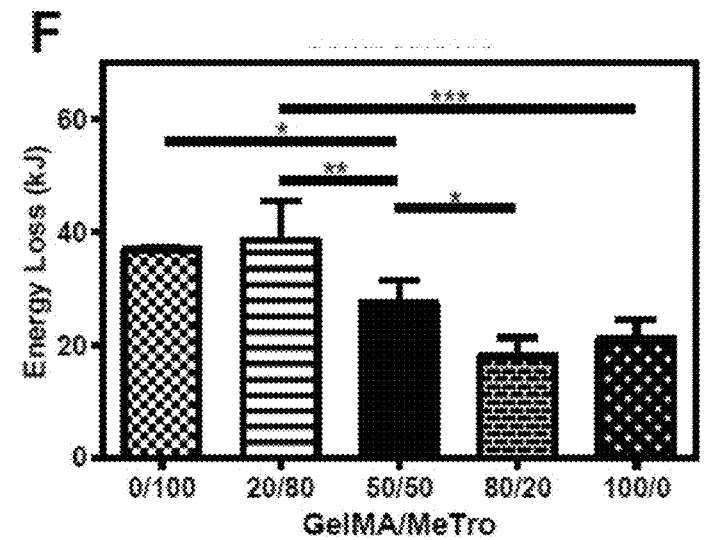
FIG. 2D-F

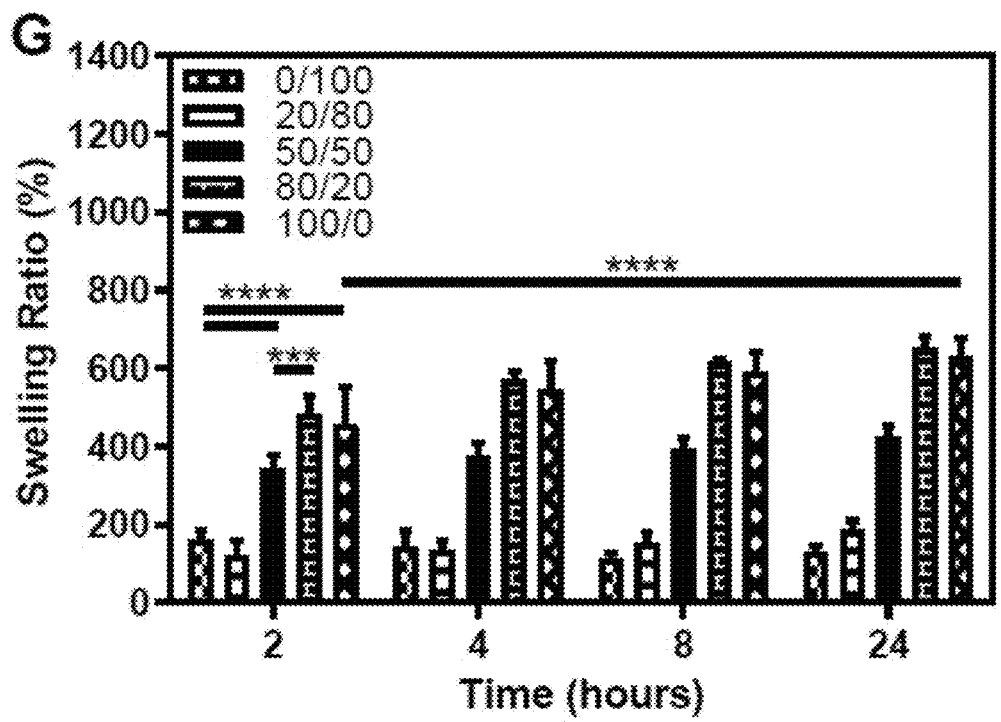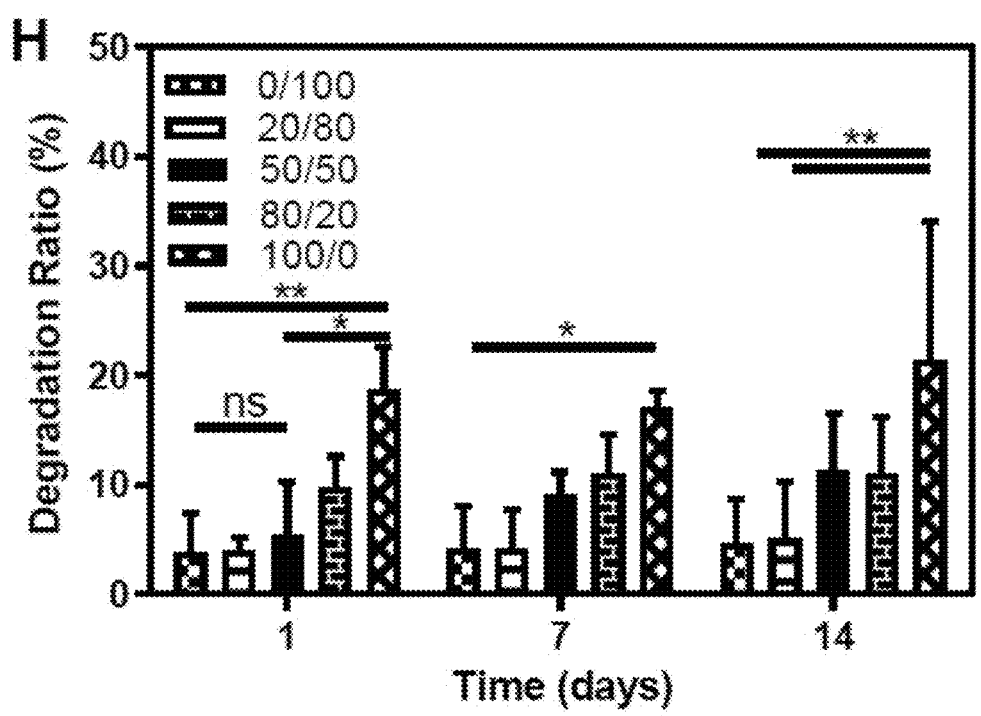
FIG. 2G-H

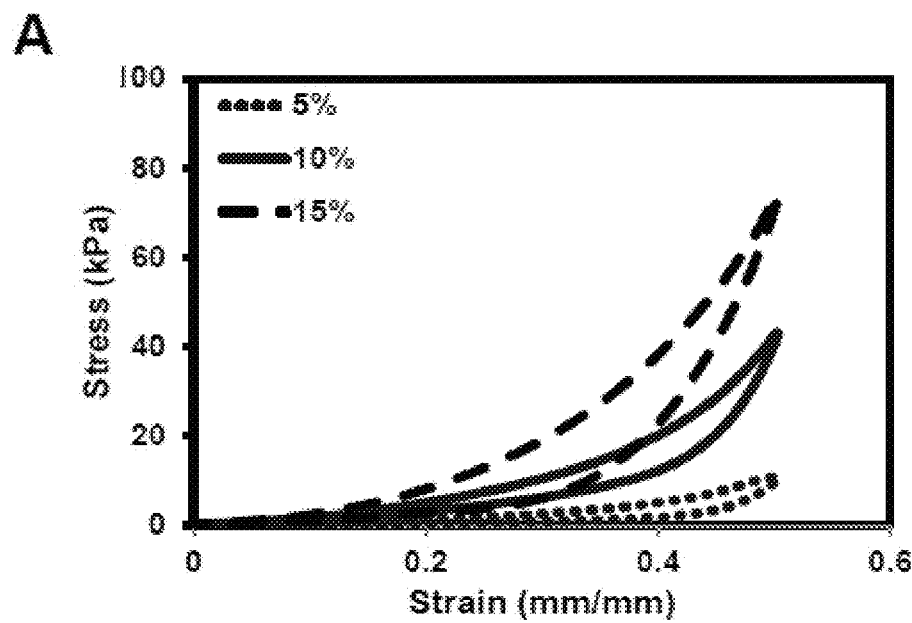
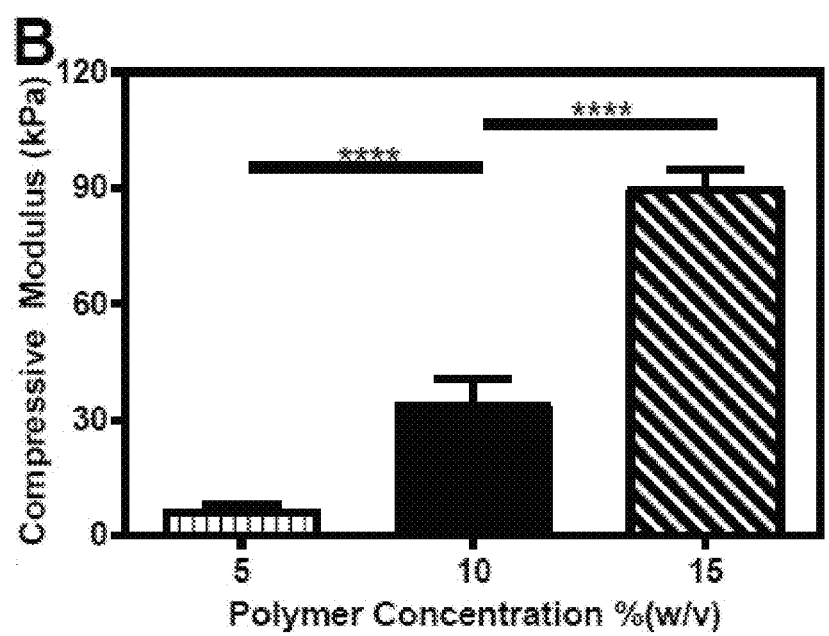
FIG. 3A-B

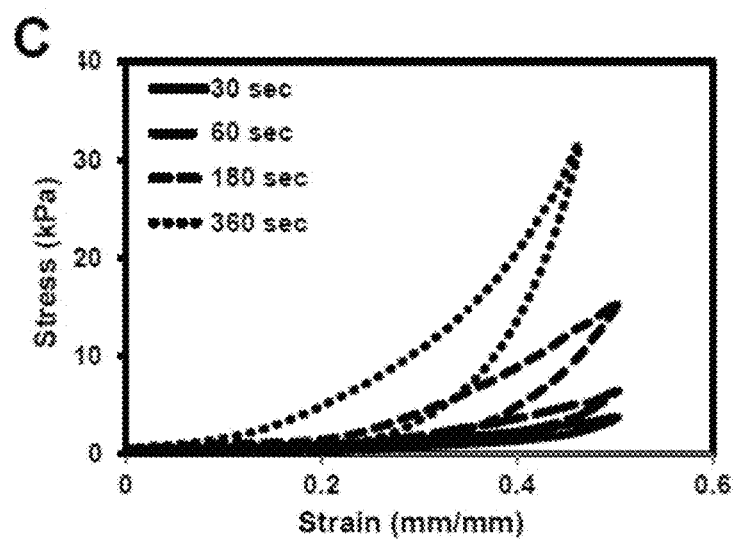
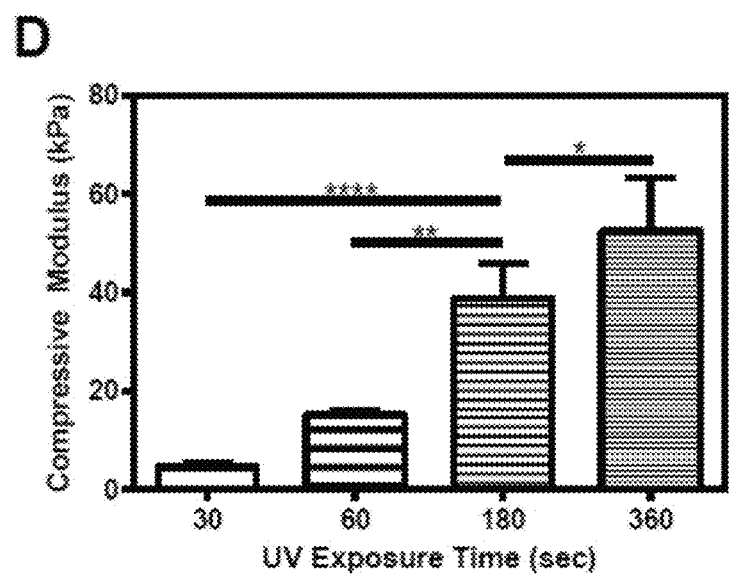
FIG. 3C-D

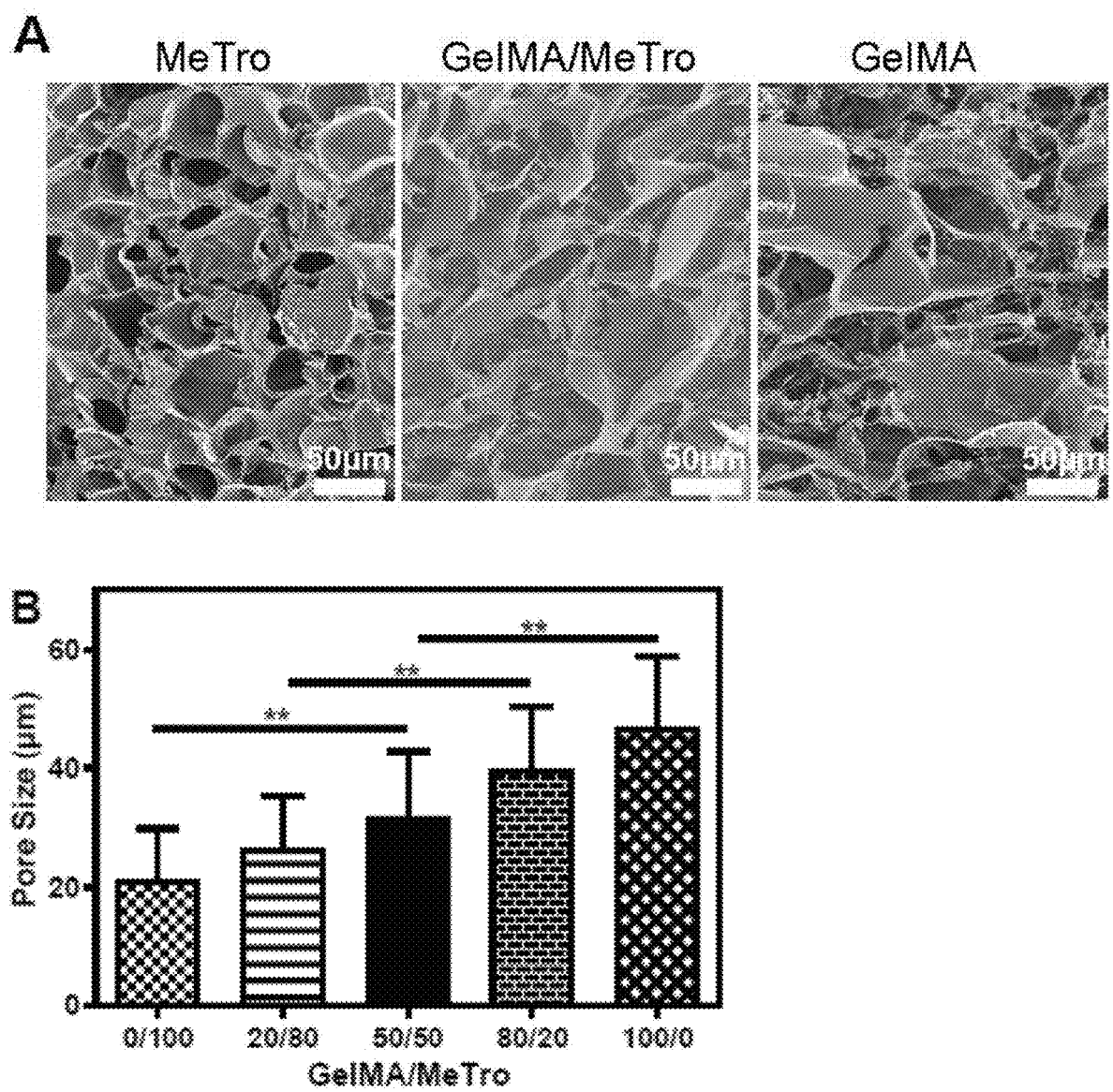
FIG. 4A-B

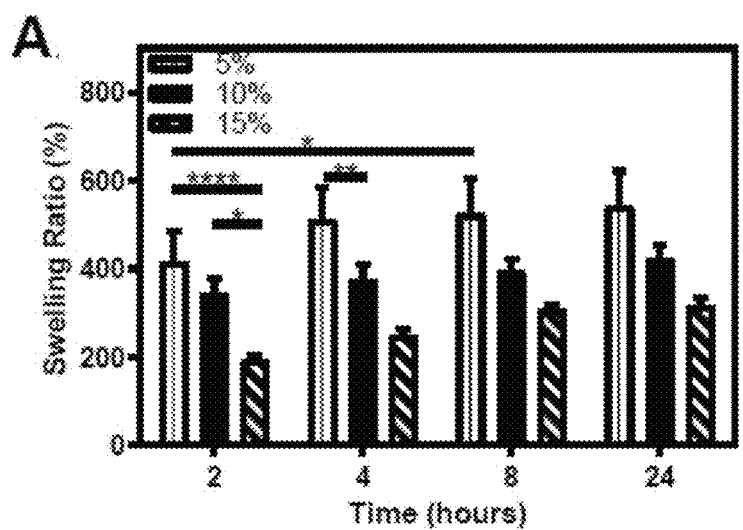
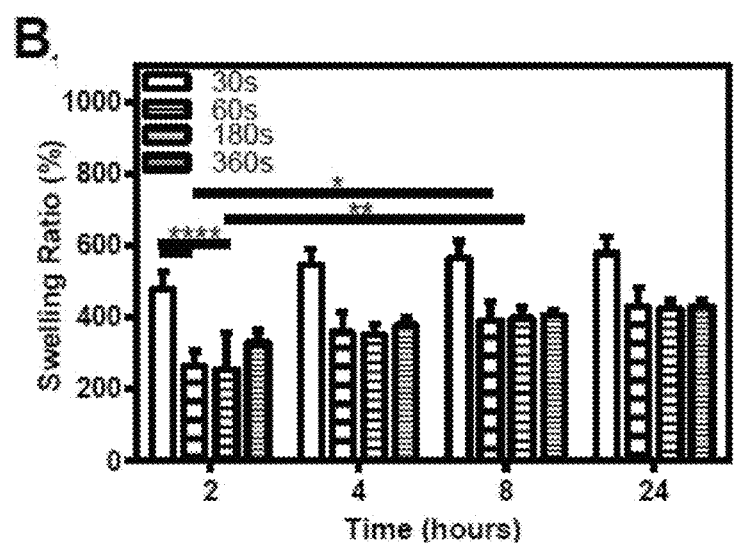
FIG. 5A-B

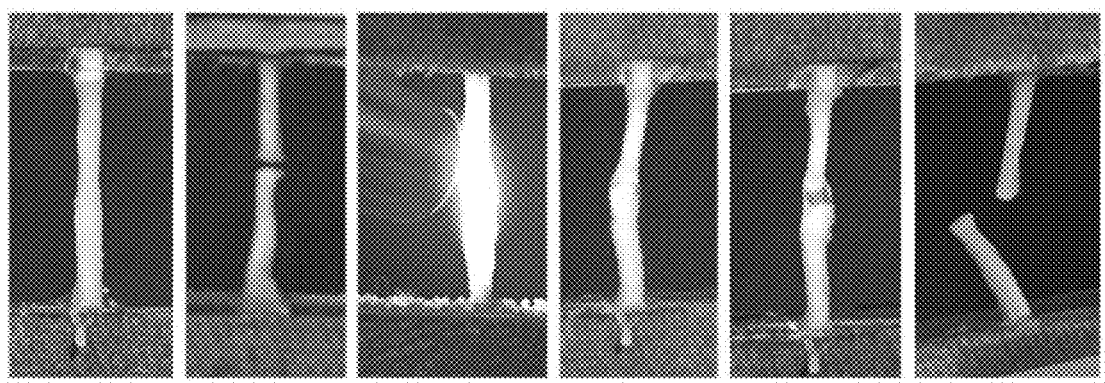
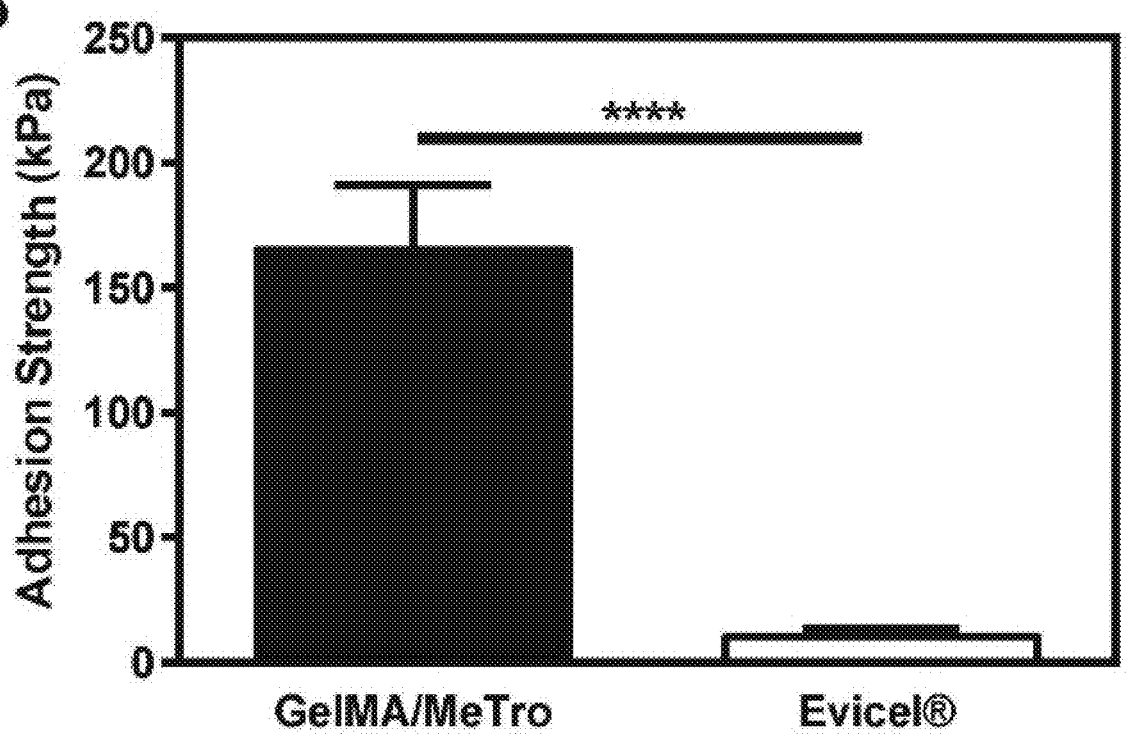
FIG. 6A-B

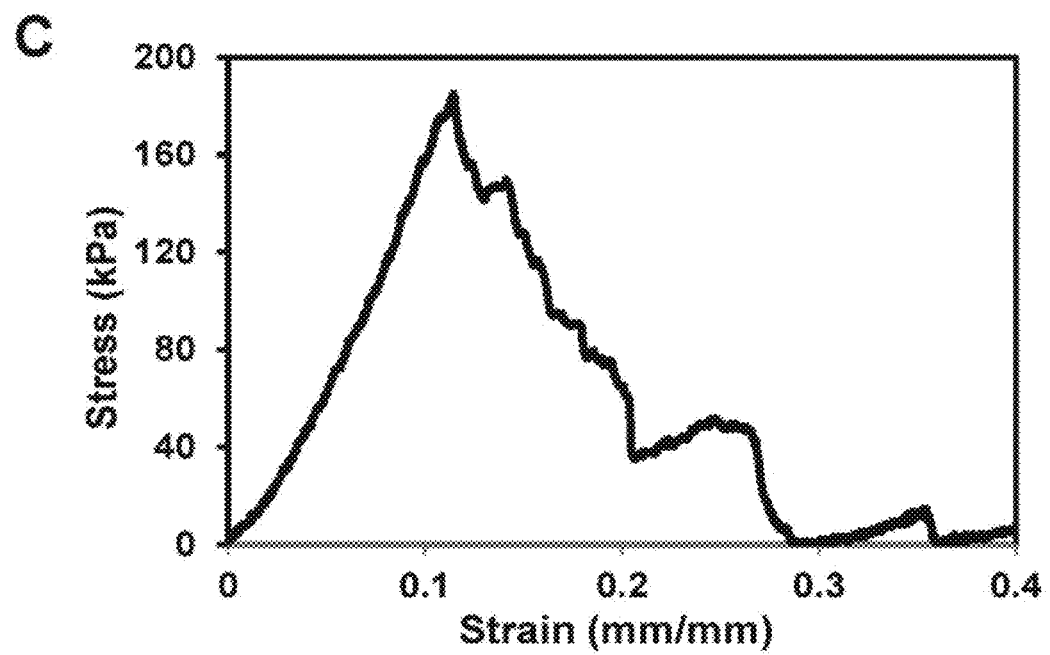
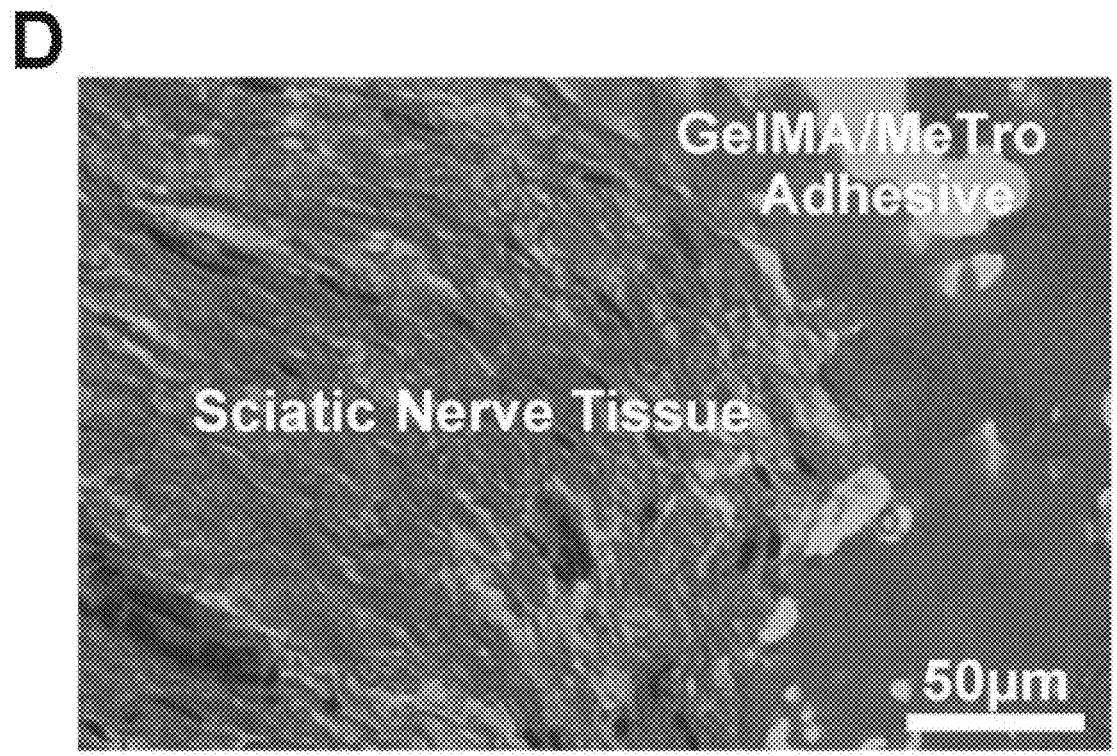
FIG. 6C-D

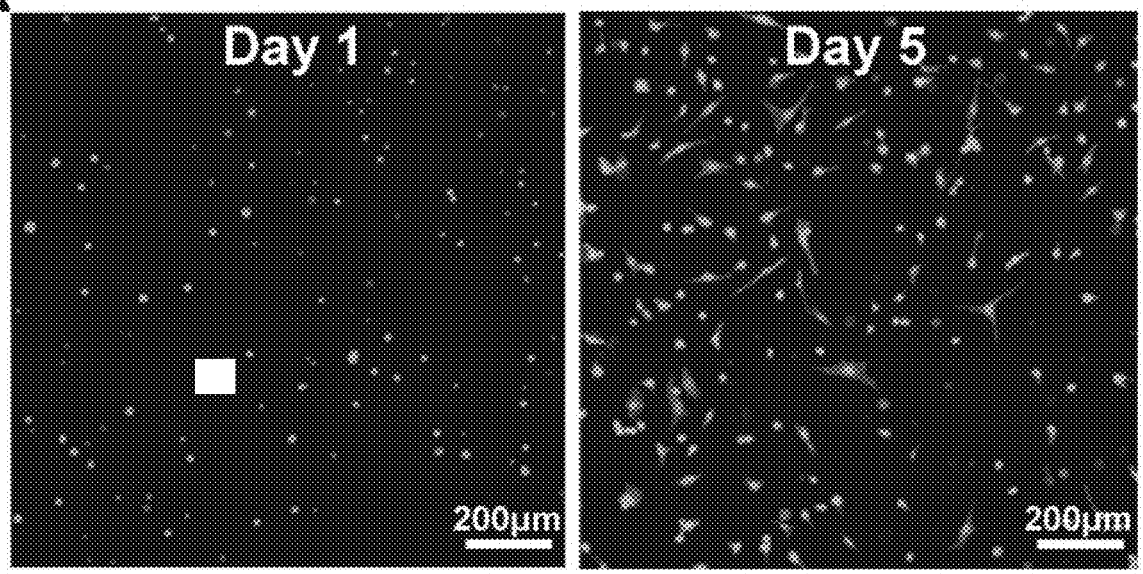
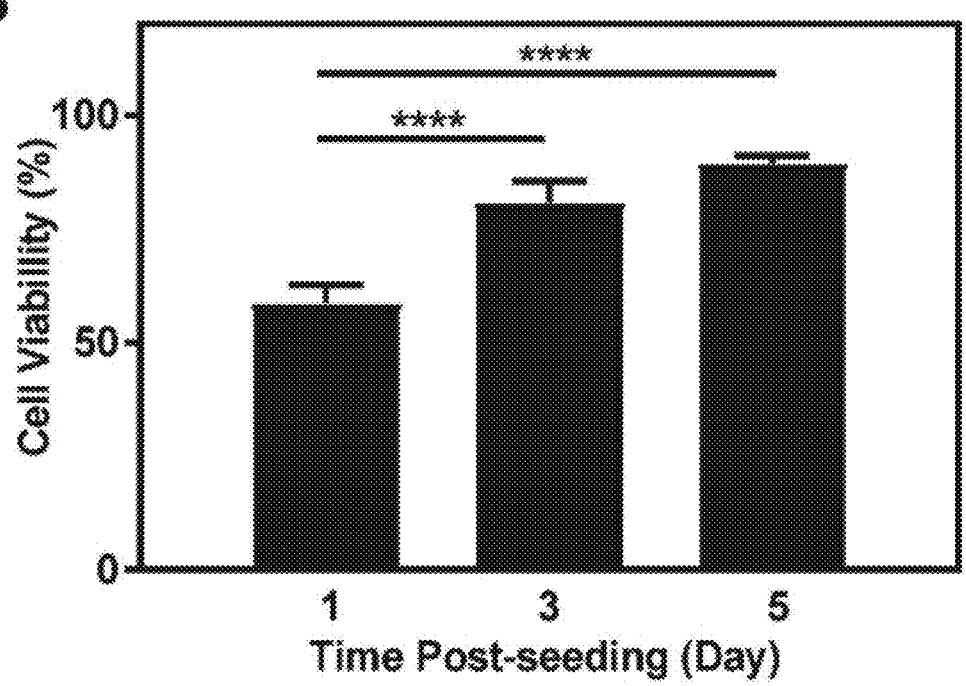
FIG. 7A-B

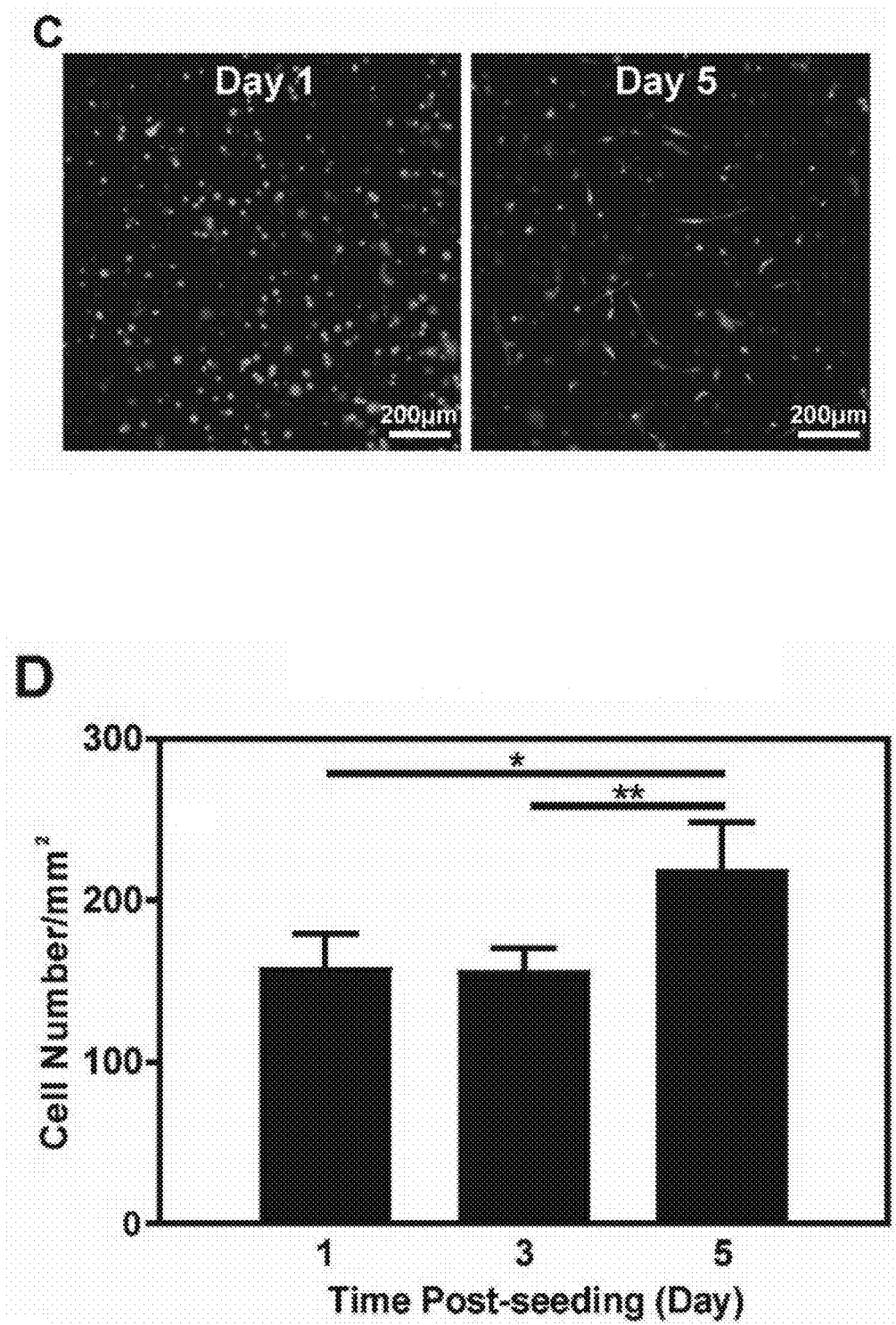
FIG. 7C-D

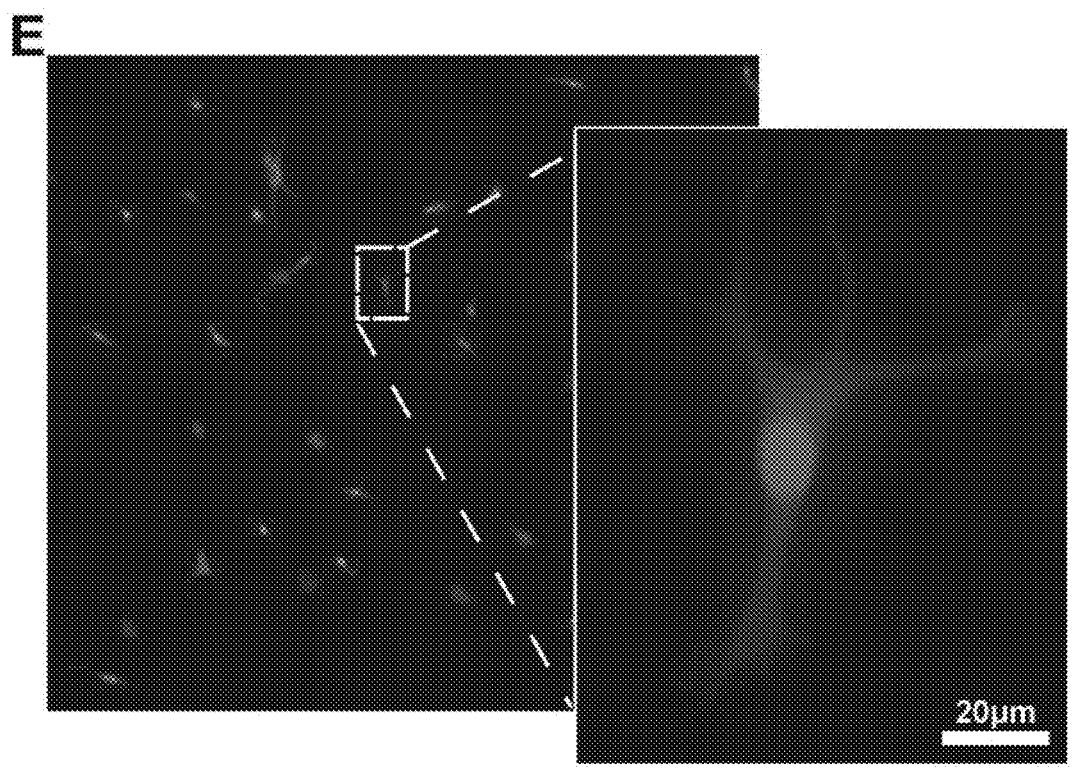
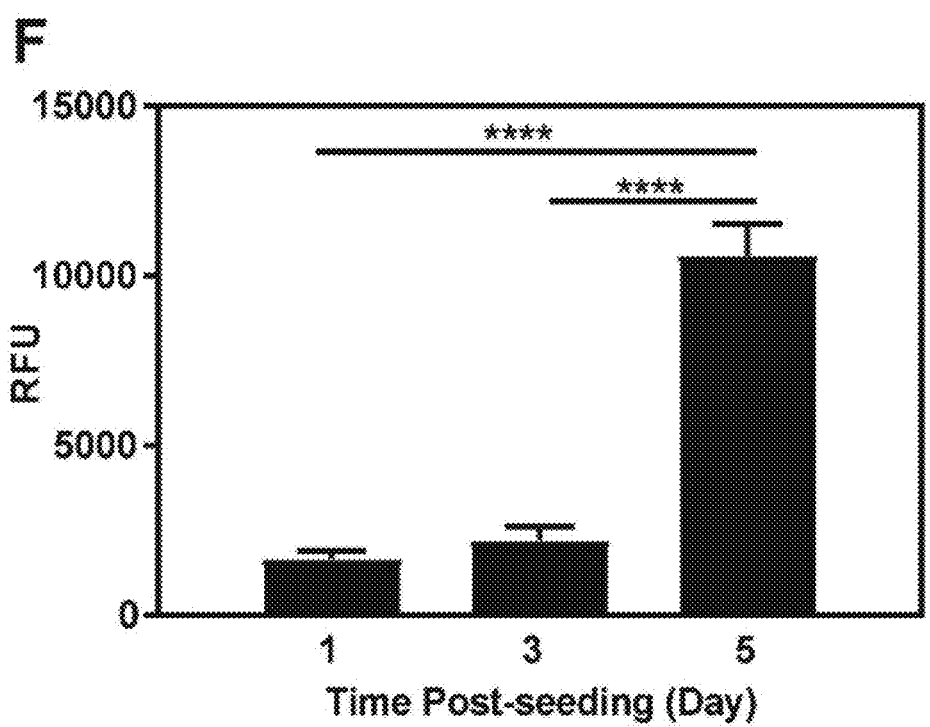
FIG. 7E-F

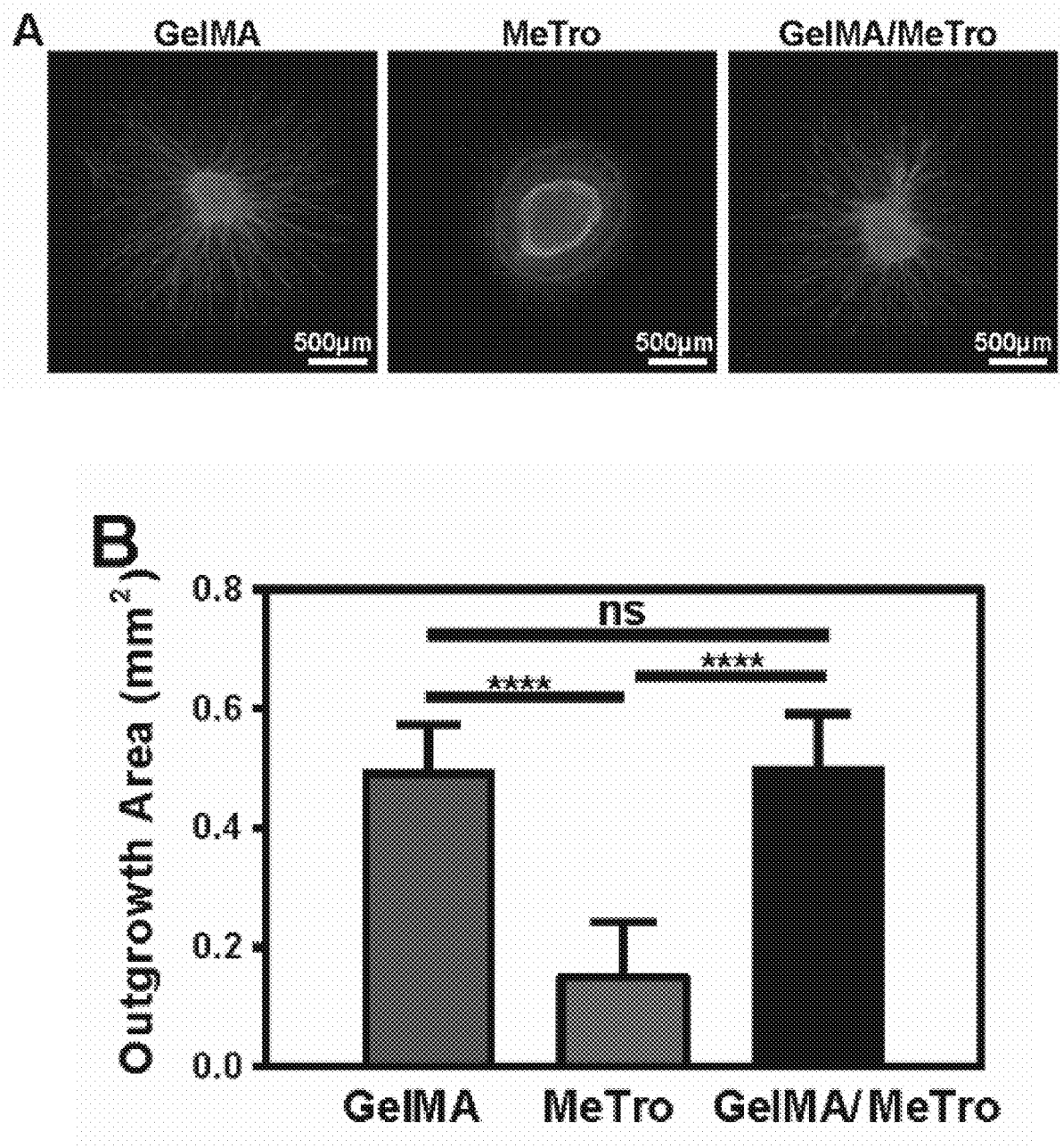
FIG. 8A-B

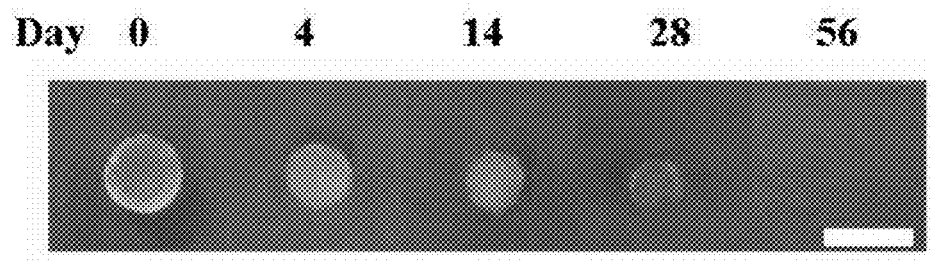
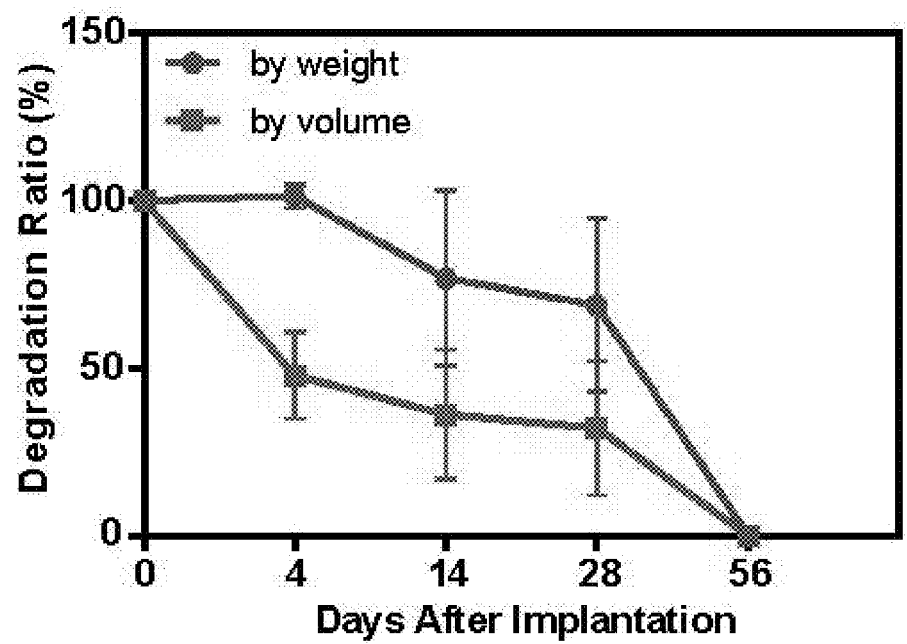
FIG. 9A-B

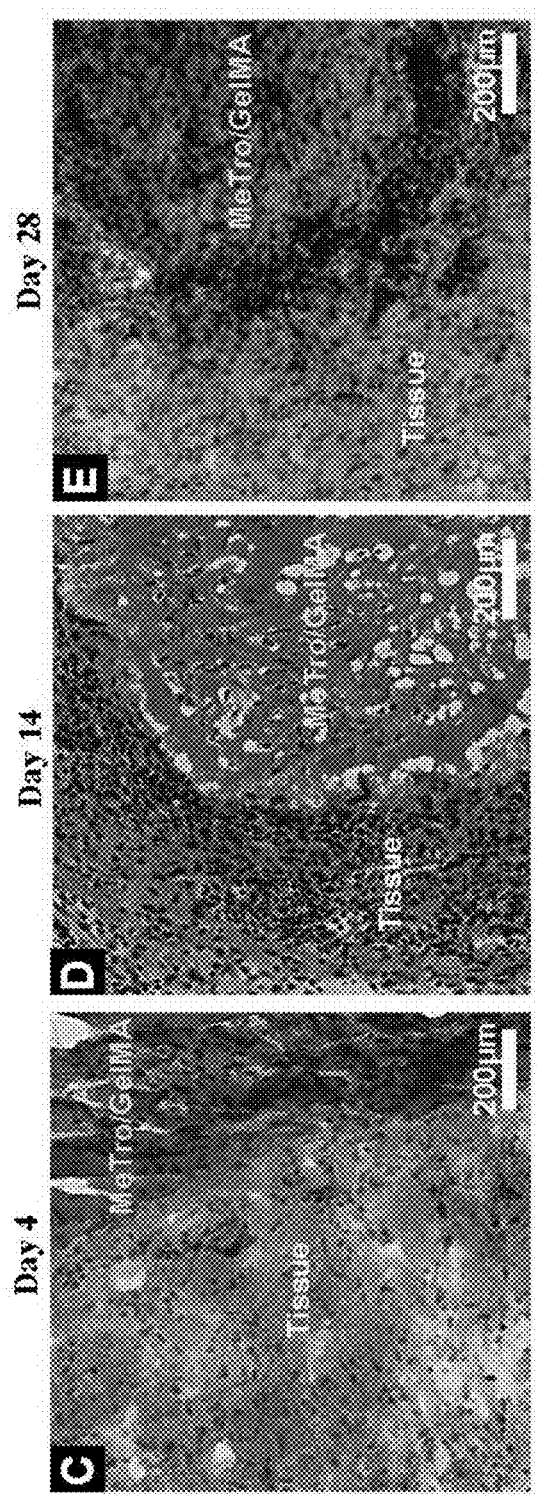
FIG. 9C-E

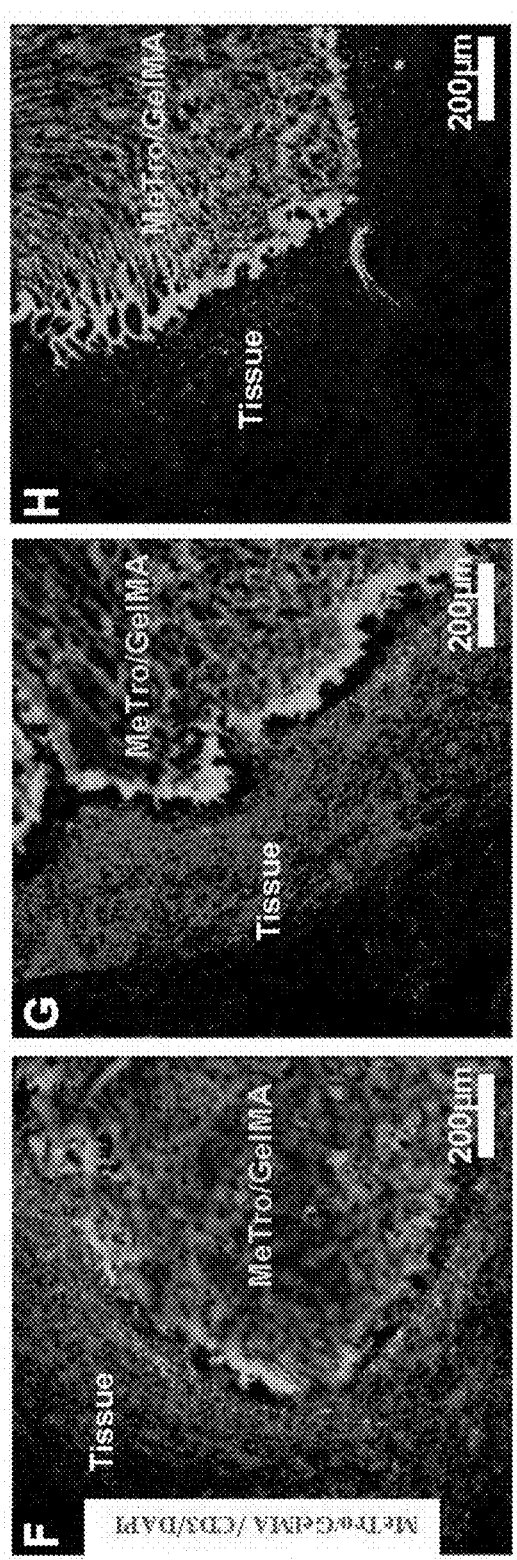
FIG. 9F-H

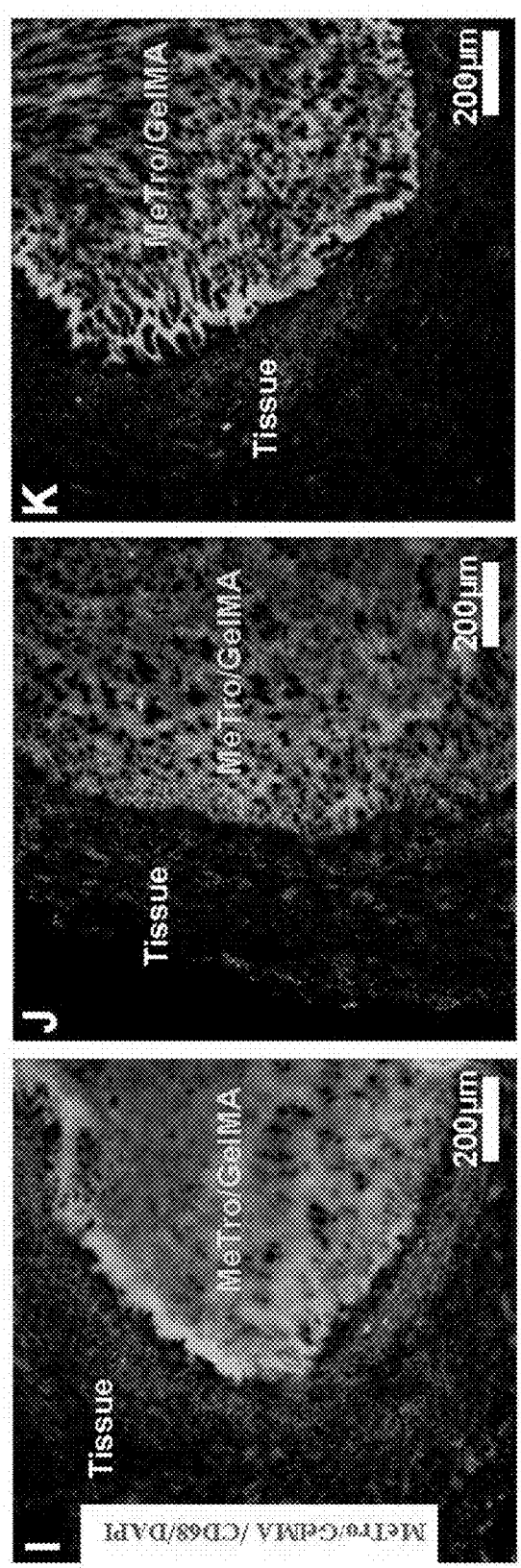
FIG. 9I-K

GELATIN/ELASTIN COMPOSITES FOR PERIPHERAL NERVE REPAIR

RELATED APPLICATION

This application claims the benefit of U.S. Provisional Application No. 62/548,899, filed on Aug. 22, 2017. The entire teachings of the above application are incorporated herein by reference.

BACKGROUND

Peripheral nerve injury (PNI) often leads to partial or complete loss of sensation, chronic pain, apraxia, and even permanent disability. Due to the slow rate of regeneration in the peripheral nervous system (PNS), surgical intervention is often required for functional recovery. Regardless of the type of surgical intervention (e.g., anastomosis or grafting), standard therapies involve the use of nylon or polypropylene sutures to mechanically stabilize and reconstruct nerves. However, previous reports have demonstrated that sutures often lead to a heightened foreign body response (FBR) and scar tissue formation, which further prevents regeneration. To reduce the dependency on sutures and the resultant FBR, fibrin glue has been used as an adjuvant for fascicle alignment and reattaching nerve endings in the clinic. Known fibrin-based glues do not actively promote regeneration, and are not mechanically robust to significantly reduce the need for sutures in the highly dynamic environment of the PNS.

The regenerative potential of the PNS can be attributed to the supportive actions of glial cells. However, the slow regeneration rate of peripheral nerves constitutes a major burden on the patient and the healthcare community, and hinders the clinical management of PNI. Previous studies have reported the incorporation of Schwann cells (SCs) into allografts in order to increase the rate of nerve regeneration. In addition, due to the important role of SCs in promoting neuronal growth in vivo, they have been used in various cell-based therapeutic strategies for PNS regeneration. Several biomaterials-based approaches have been explored as delivery systems of SCs or other glial cells to the site of PNI. Although hydrogel-based biomaterials have been widely used for SC delivery, the engineering of a cell-laden hydrogel bioadhesive has not been reported.

Suturing peripheral nerve transections is the predominant therapeutic strategy for nerve repair. However, the use of sutures can lead to scar tissue formation, hinder nerve regeneration, and prevent functional recovery. Several sutureless interventions have been proposed, including tissue laser welding (LTW), photochemical bonding (PTB), as well as the use of bioadhesives. While promising, these strategies have a number of limitations for PNS repair and clinical adoption. LTW can thermally induce damage to proximal nerve fibers, slowing functional recovery. Furthermore, LTW often requires suturing to mechanically stabilize the nerve. In contrast, PTB can only be utilized for nongap and critical size injuries. Neural glues are an attractive approach to overcome these limitations, but current compositions and formulations have not met the mechanical and adhesive properties required for sutureless repair. Specifically, fibrin-based glues have low stiffness and tissue adhesion specifically in wet and highly dynamic environment. Cyanoacrylate glues have high adhesion but lack biocompatibility and often elicit a foreign body response, they are also much stiffer than nerve tissue and do not support tissue regeneration.

There is a need for new adhesives that are neuro-supportive and possess strong adhesion to neural tissues, high ductility to undergo physiologically strain, and more specifically, there is a need for new composite hydrogel adhesive with tunable mechanical properties and degradation rates for peripheral nerve repair.

SUMMARY OF THE INVENTION

Hydrogel precursor solutions, adhesives and related materials and methods are described. The adhesives are neurosupportive and possess strong adhesion to neural tissues, and/or high ductility to undergo physiologically strain. Furthermore, they provide tunable mechanical properties and degradation rates for peripheral nerve repair.

One embodiment is a photocrosslinkable gelatin/tropoelastin-based composite with tunable physicochemical properties for peripheral nerve repair.

Another embodiment is a hydrogel precursor solution comprising a first and a second polymer, wherein the first polymer is methacrylated tropoelastin (MeTro), or a derivative thereof, and the second polymer is methacrylated gelatin (GelMA), or a derivative thereof, and a solvent.

Another embodiment is a method for nerve repair in a subject, the method comprising (1) applying a hydrogel precursor solution described herein to a location of nerve injury in the subject; and (2) crosslinking the first polymer with the second polymer.

BRIEF DESCRIPTION OF THE DRAWINGS

The patent or application file contains at least one drawing executed in color. Copies of this patent or patent application publication with color drawings will be provided by the Office upon request and payment of the necessary fee.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 1A depicts a transected nerve repaired by suturing individual fascicles and the connective tissue. FIG. 1B depicts a transected nerve repaired with a sutured-on hollow nerve conduit. FIG. 1C depicts a transected nerve repaired by photocrosslinking GelMA/MeTro composite adhesive to align fascicles and suturing of connective tissue.

FIG. 2A provides a graph of the elastic modulus of GelMA/MeTro hydrogels produced by using various GelMA/MeTro ratios at 10% (w/v) polymer concentration. FIG. 2B provides a graph of the strain at failure of GelMA/MeTro hydrogels produced by using various GelMA/MeTro ratios at 10% (w/v) polymer concentration. FIG. 2C provides a graph of the ultimate stress of GelMA/MeTro hydrogels produced by using various GelMA/MeTro ratios at 10% (w/v) polymer concentration. FIG. 2D provides a graph of representative compressive stress-strain curves for GelMA/MeTro hydrogels produced by using various GelMA/MeTro ratios at 10% (w/v) polymer concentration.

FIG. 2E provides a graph of the compressive modulus of GelMA/MeTro hydrogels produced by using various GelMA/MeTro ratios at 10% (w/v) polymer concentration. FIG. 2F provides a graph of the energy loss of GelMA/MeTro hydrogels at varying GelMA/MeTro ratios and 10% total polymer concentrations. FIG. 2G provides a graph of the swelling ratio of engineered hydrogels (produced by using various GelMA/MeTro ratios at 10% (w/v) polymer concentration) after 2, 4, 8, and 24 h incubation in DPBS. FIG. 2H provides a graph of the degradation ratio of engineered hydrogels (produced by using various GelMA/MeTro ratios at 10% (w/v) polymer concentration) in 5% FBS in DPBS on days 1, 7, and 14. All the hydrogels were formed by using 180 s crosslinking time. (ns: $p>0.05$, $*p<0.05$, $p<0.01$, $*p<0.001$, $****p<0.0001$).

FIG. 3A provides a graph of representative compressive stress-strain curves of 50/50 GelMA/MeTro composite hydrogels produced with varying polymer concentrations. FIG. 3B provides a graph of the compressive modulus for 50/50 GelMA/MeTro composite hydrogels produced with varying total polymer concentration and 180 s crosslinking time. FIG. 3C provides a graph of representative compressive stress-strain curves for 50/50 GelMA/MeTro composite hydrogels at 10% (w/v) total polymer concentration produced at varying crosslinking times ($*p<0.05$, $p<0.01$, $**p<0.0001$). FIG. 3D provides a graph of compressive modulus for 50/50 GelMA/MeTro composite hydrogels at 10% (w/v) total polymer concentration produced at varying crosslinking times ($*p<0.05$, $p<0.01$, $**p<0.0001$).

FIG. 4A provides representative SEM images from the cross-sections of MeTro, 50/50 GelMA/MeTro, and GelMA hydrogels produced by using 10% (w/v) total polymer concentration and 180 s crosslinking. FIG. 4B provides a graph of the average pore sizes of composite hydrogels produced by varying GelMA/MeTro ratios at 10% polymer concentration, calculated from SEM images (n=15) such as those shown in FIG. 4A ($**p<0.01$).

FIG. 5A provides a graph of swelling ratios of GelMA/MeTro composite hydrogels after 2, 4, 8, and 24 h for 50/50 GelMA/MeTro composite hydrogels produced with varying total polymer concentration and 180 s crosslinking time. FIG. 5B provides a graph of swelling ratios after 2, 4, 8, and 24 h for 50/50 (w/w) GelMA/MeTro composite hydrogels at 10% (w/v) total polymer concentration produced at various crosslinking times ($*p<0.05$, $p<0.01$, $**p<0.0001$).

FIG. 6A depicts ex vivo nerve anastomosis using GelMA/MeTro hydrogel adhesives. Left to right: representative photographs of clamped intact nerve with a gauge length of 12 mm, severed nerve, photocrosslinking GelMA/MeTro composite (50/50 ratio at 10% polymer concentration) between nerve endings, anastomosed nerve, initial strain, and broken nerve. FIG. 6B provides a graph of the adhesion strength of a nerve glued by a 50/50 GelMA/MeTro composite adhesive and Evicel® (n=6). FIG. 6C provides a graph of a representative stress-strain curve of anastomosed nerves using a 50/50 GelMA/MeTro composite at 10% total polymer concentration and 180 s crosslinking time. FIG. 6D provides an image of representative H&E staining from a cross-sectional area of the GelMA/MeTro composite at the interface of an anastomosed sciatic nerve ($****p<0.0001$).

FIG. 7A provides an image of in vitro SC 3D encapsulation in a 20/80 GelMA/MeTro hydrogel at 10% total polymer concentration. Representative calcein-AM (green)/ethidium homodimer (red) stained images from cell-laden hydrogels after 1 and 5 days of culture. FIG. 7B provides a quantification of cell viability after 1, 3, and 5 days post-encapsulation. FIG. 7C provides an image of in vitro SC 3D encapsulation in a 20/80 GelMA/MeTro hydrogel at 10% total polymer concentration. Representative phalloidin (green)/DAPI (blue) stained images from cell-laden hydrogels after 1 and 5 days of encapsulation. FIG. 7D provides a quantification of total cell number by nuclei counting after 1, 3, and 5 days of encapsulation. FIG. 7E provides immnocytofluorescent images for the expression of Schwann cell marker S100 (red)/DAPI (blue) 5 days after encapsulation. FIG. 7F provides a quantification of metabolic activity (RFU: relative fluorescence intensity) by PrestoBlue 1, 3, and 5 days' post encapsulation ($*p<0.05$, $p<0.01$, $**p<0.0001$).

FIG. 8A regards in vitro dorsal root ganglia 3D encapsulation within GelMA/MeTro hydrogels. Representative β-3-tubulin (purple) immnocytofluorescent images of encapsulated DRGs in GelMA, MeTro, 50/50 GelMA/MeTro at 10% (w/v) total polymer concentration and 30 sec UV exposure. FIG. 8B provides a quantification of total outgrowth area from MATLAB image analysis (n>4) with regard to the in vitro dorsal root ganglia 3D encapsulation within GelMA/MeTro hydrogels.

FIG. 9A provides representative images of in vivo degradation of GelMA/MeTro hydrogels (using a rat subcutaneous model) on days 0, 4, 14, 28 and 56 post-implantation. FIG. 9B provides a graph of the in vivo degradation of GelMA/MeTro hydrogels (using a rat subcutaneous model) based on weight and volume loss of the implants (n=3). FIG. 9C provides an image of H&E staining of GelMA/MeTro sections (hydrogels with the surrounding tissue) after 4 days post-implantation (using a rat subcutaneous model). FIG. 9D provides an image of H&E staining of GelMA/MeTro sections (hydrogels with the surrounding tissue) after 14 days post-implantation (using a rat subcutaneous model). FIG. 9E provides an image of H&E staining of GelMA/MeTro sections (hydrogels with the surrounding tissue) after 28 days post-implantation, showing excellent tissue integration (using a rat subcutaneous model). FIG. 9F provides an image of immunohistofluorescent staining of subcutaneously implanted GelMA/MeTro hydrogels demonstrating no significant local lymphocyte infiltration (CD3, red) at day 4 (using a rat subcutaneous model). FIG. 9G provides an image of immunohistofluorescent staining of subcutaneously implanted GelMA/MeTro hydrogels demonstrating no significant local lymphocyte infiltration (CD3, red) at day 14 (using a rat subcutaneous model). FIG. 9H provides an image of immunohistofluorescent staining of subcutaneously implanted GelMA/MeTro hydrogels demonstrating no significant local lymphocyte infiltration (CD3, red) at day 28 (using a rat subcutaneous model). FIG. 9I provides an image of immunohistofluorescent staining against macrophages (CD68, red; GelMA/MeTro composites are green and cell nuclei (DAPI) are in blue) at day 4 (using a rat subcutaneous model). FIG. 9J provides an image that shows a significant reduction (relative to day 4 as seen in FIG. 9I) of immunohistofluorescent staining against macrophages (CD68, red; GelMA/MeTro composites are green and cell nuclei (DAPI) are in blue) after day 14. FIG. 9K provides an image that shows a significant reduction (relative to day 4 and 14 as seen in FIGS. 9I and 9J) of immunohistofluorescent staining against macrophages (CD68, red; GelMA/MeTro composites are green and cell nuclei (DAPI) are in blue) after day 28.

DETAILED DESCRIPTION

Figure 1D:
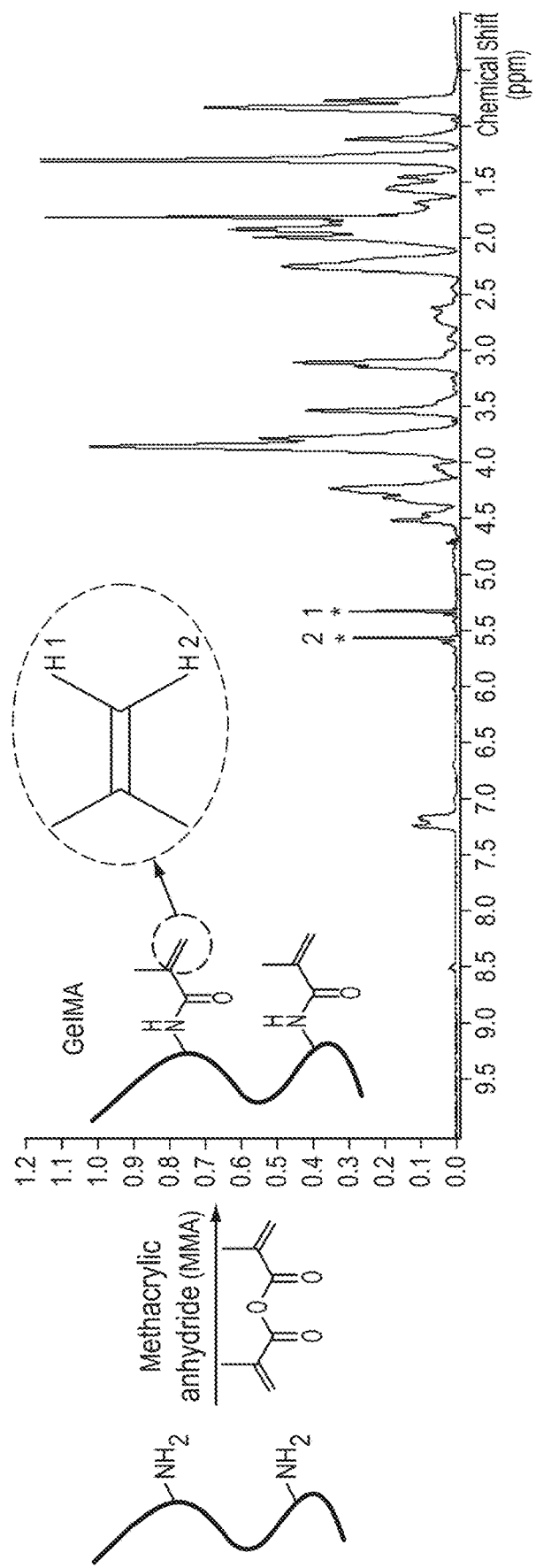
FIG. 1D depicts the methacrylol substitution of gelatin to form GelMA, conformed using $^1$H NMR, the $^1$H NMR spectra shown on the right-hand side.

A description of example embodiments follows.

The hydrogel precursor solutions described herein provide for new adhesives that allow for improved properties such as being neuro-supportive (e.g., supportive of neurite extension and Schwann cell participation), possessing strong adhesion to neural tissues, allowing tunable mechanical properties (e.g., high resilience, high elasticity) and/or tunable degradation rates for peripheral nerve repair. The hydrogel precursor solutions have been found to be fast polymerizable (e.g. rapidly crosslinked) by using light for simple application. They can provide for stronger tissue adhesion compared to commercially available fibrin-based glues and they can further be used as a cell deliver vehicle. Additionally, in certain embodiments the hydrogel precursor solutions described herein can be biocompatible and/or biodegradable.

Commercial applications include, but are not limited to, the use in the clinic as an alternative to fibrin-based glues for nerve repair, the use to fill the lumen of nerve conduits (cell-laden or not), the use to promote regeneration and repair of damaged nerve tissue, the use as neural adhesive, e.g., neural adhesive for nerve anastomosis, the use as cell delivery vehicle, and the use as nerve conduit filling material.

A first embodiment is a hydrogel precursor solution comprising a first and a second polymer, wherein the first polymer is methacrylated tropoelastin (MeTro), or a derivative thereof, and the second polymer is methacrylated gelatin (GelMA), or a derivative thereof, and a solvent.

In an aspect of the first embodiment, the solvent is distilled water or saline solution.

Typically, the saline solution is an aqueous solution; however, neutral pH, and low salt solutions, can also be dissolved in different alcohols. The latter case does not typically support cell-delivery but can function as an adhesive.

In another aspect of the first embodiment or any of the foregoing aspects of the first embodiment, the hydrogel precursor solution has a total polymer concentration of between about 5% and about 25% (w/v).

As used herein, "between" a first and second value means the first value, all values from the first value to the second value, and the second value. As used herein, "about" a given value, refers to the value plus and minus ten percent of the value.

While higher total polymer concentrations can be desirable for increasing strength of the resulting polymer material and/or higher adhesion, lower total polymer concentrations can be desirable to allow better cell growth. Total polymer concentration can be between about 5% and about 25% (w/v). In specific embodiments, it can be between about 5% and about 20% (w/v). In further specific embodiments, it can be between about 5% and about 15% (w/v). In further specific embodiments, it can be between about 5% and about 10% (w/v). In further specific embodiments, it can be between about 10% and about 25% (w/v). In further specific embodiments, it can be between about 10% and about 20% (w/v). In further specific embodiments, it can be between about 15% and about 25% (w/v). In further specific embodiments, it can be between about 15% and about 20% (w/v).

In another aspect of the first embodiment or any of the foregoing aspects of the first embodiment, the ratio of the first to second polymer is between 0/100 to 100/0. In a more specific aspect, the ratio of the first to second polymer is between about 10/90 to about 90/10.

Higher MeTro concentrations typically allow for longer degradation and preventing neurite growth and can be useful as a conduit or shell around a filler material. A neural wrap may reduce the risk of neuromas by preventing neurite extension and isolating the injury site from surrounding tissue. Higher GelMA concentrations typically allow for improved cell spreading at the expense of mechanics and degradation.

The ratio of the first to second polymer can be between 0/100 and 100/0. In specific embodiments, it can be between about 10/90 to 90/10. In further specific embodiments, it can be between about 20/80 to about 80/20. In further specific embodiments, it can be between about 30/70 to about 70/30. For example, the ration can be 0/100, 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, 95/5, or 100/0.

In another aspect of the first embodiment or any of the foregoing aspects of the first embodiment, the methacrylated tropoelastin was prepared by methacrylation of human tropoelastin isoform SHELΔ26A.

In another aspect of the first embodiment or any of the foregoing aspects of the first embodiment, the methacrylated gelatin was prepared by methacrylation of fish gelatin.

In another aspect of the first embodiment or any of the foregoing aspects of the first embodiment, the solution comprises a light activated photoinitiator in an amount suitable to form a hydrogel from the solution upon activation with UV and/or visible light.

In another aspect of the first embodiment or any of the foregoing aspects of the first embodiment, the solution comprises a light activated photoinitiator in an amount from about 0.1% to about 1% (w/v). In a specific aspect, the amount is from about 0.25% to about 0.75% (w/v). In a further specific aspect, the amount is about 0.5% (w/v). In a further specific aspect, the amount is 0.5% (w/v).

In another aspect of the first embodiment or any of the foregoing aspects of the first embodiment, the solution comprises a light activated photoinitiator which is a UV or visible light activated photoinitiator.

In another aspect of the first embodiment or any of the foregoing aspects of the first embodiment, the solution comprises a light activated photoinitiator which is 2-hydroxy-4'-(2-hydroxyethoxy)-2-methylpropiophenone, Eosin Y (2-(2,4,5,7-tetrabromo-6-oxido-3-oxo-3H-xanthen-9-yl)benzoate), or lithium phenyl-2,4,6-trimethylbenzoylphosphinate.

In another aspect of the first embodiment or any of the foregoing aspects of the first embodiment, the solution further comprises Schwann cells (SCs).

It is believed that the materials described here support cell growth because of integrins, Arg-Gly-Asp (RGD) domains in GelMA, and avb3 integrins in MeTro. Typically, it is desirable that the cell-laden hydrogel precursor solutions possess a low viscosity, ensuring low shear stress during injection, and homogenous distribution of SC payload.

In another aspect of the first embodiment or any of the foregoing aspects of the first embodiment, the solution contains the Schwann cells at a concentration of about $1\times10^6$ cells/ml to about $30\times10^6$ cells/ml. In a specific aspect, the solution contains the Schwann cells at a concentration of about $1\times10^6$ cells/ml to about $20\times10^6$ cells/ml. In a specific aspect, the solution contains the Schwann cells at a concentration of about $1\times10^6$ cells/ml to about $10\times10^6$ cells/ml. In a specific aspect, the solution contains the Schwann cells at a concentration of about $2\times10^6$ cells/ml to about $20\times10^6$ cells/ml. In a specific aspect, the solution contains the Schwann cells at a concentration of about $2\times10^6$ cells/ml to about $10\times10^6$ cells/ml. In a specific aspect, the solution contains the Schwann cells at a concentration of about $4\times10^6$ cells/ml to about $6\times10^6$ cells/ml. In a specific aspect, the solution contains the Schwann cells at a concentration of $4\times10^6$ cells/ml to $6\times10^6$ cells/ml. In a specific aspect, the solution contains the Schwann cells at a concentration of about $5\times10^6$ cells/ml. In a specific aspect, the solution contains the Schwann cells at a concentration of $5\times10^6$ cells/ml.

A second embodiment is a method for nerve repair in a subject, the method comprising (1) applying a hydrogel precursor solution described herein (for example, a hydrogel precursor solution of the first embodiment or of any of the foregoing aspects thereof) to a location of nerve injury in the subject; and (2) crosslinking the first polymer with the second polymer.

Typically, the subject is a mammal, for example, a human, mouse, rat, guinea pig, dog, cat, horse, cow, pig, or non-human primate, such as a monkey, chimpanzee, baboon or rhesus. More typically, the subject is a human.

In another aspect of the second embodiment, the method further comprises filling the lumen of nerve conduits in the location of nerve injury with the hydrogel precursor solution.

In another aspect of the second embodiment or any of the foregoing aspects of the second embodiment, the location of nerve injury is in a space between nerve ends in need of reconnecting, and applying the hydrogel precursor solution comprises filling the space between the nerve ends with the hydrogel precursor solution.

In another aspect of the second embodiment or any of the foregoing aspects of the second embodiment, more than one formulation ratio of first and second polymer is utilized to form a core and shell nerve guidance conduit.

The core of a nerve guidance conduit, may be designed to be more degradable using a higher concentration of GelMA surrounded by a stronger, less degradable shell with higher ratio of MeTro.

In another aspect of the second embodiment or any of the foregoing aspects of the second embodiment, the core is formed using the hydrogel precursor solution with a concentration of gelatin methacryloyl which is higher than in the shell.

In another aspect of the second embodiment or any of the foregoing aspects of the second embodiment, the shell is formed using the hydrogel precursor solution with a concentration of methacryloyl-substituted tropoelastin which is higher than in the core.

A third embodiment is a material prepared by reacting a hydrogel precursor solution described herein (for example, a hydrogel precursor solution of the first embodiment or of any of the foregoing aspects thereof). In an aspect of the third embodiment, reacting is crosslinking. In a specific aspect, crosslinking is achieved by exposure to UV or visible light.

A fourth embodiment is cell delivery system, comprising a hydrogel precursor solution described herein (for example, a hydrogel precursor solution of the first embodiment or of any of the foregoing aspects thereof) or a material (for example, of the third embodiment or any of the foregoing aspects thereof), wherein the solution or material contains cells such as Schwann cells.

A fifth embodiment is a nerve guidance conduit, comprising a shell and a core, wherein the core is formed by reacting a first hydrogel precursor solution described herein (for example, a hydrogel precursor solution of the first embodiment or of any of the foregoing aspects thereof) and the shell is formed by reacting a second hydrogel precursor solution described herein (for example, a hydrogel precursor solution of the first embodiment or of any of the foregoing aspects thereof).

In an aspect of the fifth embodiment, the first and second hydrogel precursor solutions are different.

In another aspect of the fifth embodiment or any of the foregoing aspects of the fifth embodiment, the core is formed before the shell is formed.

In another aspect of the fifth embodiment or any of the foregoing aspects of the fifth embodiment, the core is formed using a hydrogel precursor solution with a concentration of gelatin methacryloyl which is higher than in the shell.

In another aspect of the second embodiment or any of the foregoing aspects of the second embodiment, the shell is formed using a hydrogel precursor solution with a concentration of methacryloyl-substituted tropoelastin which is higher than in the core.

Example

1. Introduction

Hydrogels were synthesized by photocrosslinking two naturally derived polymers, gelatin-methacryloyl (GelMA) and methacryloyl-substituted tropoelastin (MeTro). The mechanical properties of the composites can be tuned by varying the GelMA/MeTro ratio. GelMA/MeTro hydrogels exhibited 15-fold higher adhesive strength to nerve tissue, when compared to fibrin ex vivo. Furthermore, the composites were shown to support SC growth, as well as neurite extension and glial cell participation in vitro, which are essential for nerve regeneration. Subcutaneously implanted hydrogels exhibited high biocompatibility and slower degradation rates in vivo, as compared to pure GelMA, which highlights its potential to support the growth of slowly regenerating nerves. Thus, GelMA/MeTro composites may be used in the clinic, to regenerate nerves and reduce the need for sutures during nerve reconstruction.

It is desirable that a hydrogel adhesive for nerve tissue repair: 1) support the three-dimensional (3D) growth and participation of SCs, 2) provide high adhesive strength to neural tissue to reduce the need for suturing, 3) enable neurite extension, 4) possess mechanical reliance to withstand physiological strain, 5) degrade at a rate to allow time for tissue regeneration, and 6) minimize FBR. GelMA and (MeTro are biopolymers derived from the ECM proteins collagen and tropoelastin, respectively (see N. Annabi et al. *Biomaterials* 2013, 34, 5496; and J. W. Nichol et al. *Biomaterials* 2010, 31, 5536.). Although GelMA hydrogels have been shown to exhibit high biocompatibility in vitro and in vivo, they suffer from low elasticity and rapid degradation rates. On the other hand, MeTro hydrogels possess high elasticity and stiffness, and comparatively slower in vivo degradation rates. However, the high mechanical stiffness of MeTro limits their application for 3D cell encapsulation.

GelMA/MeTro hydrogel adhesives with tunable physicochemical properties for neural tissue engineering applications were developed. The incorporation of two biopolymers with distinct biophysical and biochemical characteristics enabled the engineering of hydrogels with a wide spectrum of physicochemical properties. The physical properties of the engineered hydrogels, including porosity, stiffness, elasticity, swellability, and in vitro and in vivo degradation rates were evaluated. In addition, the efficacy of GelMA/MeTro composites as adhesives for nerve anastomosis ex vivo was examined. The ability of this material to support the viability and proliferation of SCs, and to promote the extension of PNS neurons encapsulated within the composite hydrogels was also investigated. The biodegradability and immunogenicity of GelMA/MeTro hydrogels via subcutaneous implantation in vivo was also evaluated.

2. Results & Discussion

Conventional therapies for the treatment of PNI only lead to functional recovery in ~50% of cases. Depending upon the severity of a nerve injury, different therapeutic strategies are used to achieve the highest degree of functional recovery. For instance, distal and proximal nerve stumps are often sutured end-to-end for nerve transections (FIG. 1A). In contrast, critical gaps greater than 2 cm, are generally treated using autografts and allografts to prevent excessive tension. Although autografts still constitute the current gold standard to restore function in large nerve defects, artificial nerve conduits and decellurized neural tissue (AxoGen, Inc.) are increasingly being used to overcome limited tissue availability (FIG. 1B). For instance, collagen-based materials such as NeuraGen®, NeuroFlex™, NeuroMatrix™, Neura-Wrap™, and NeuroMend™, have been approved by the Food and Drug Administration (FDA) to be used in the clinic for the treatment of PNI. However, these approaches still require extensive use of nylon or polypropylene sutures to ensure stable attachment to the native tissue. Here, a multifunctional composite hydrogel adhesive was engineered that can be used to reduce the use of sutures by providing high adhesion to neural tissues (FIG. 1C), and to promote neuronal regeneration by supporting the proliferation of glial cells.

2.1 Synthesis and Fabrication of GelMA/MeTro Hydrogels

To design and engineer a multifunctional hydrogel adhesive that can be used for the treatment of PNI, recombinant human tropoelastin and gelatin were methacrylated to form the photocrosslinkable biopolymers GelMA and MeTro. GelMA/MeTro composite hydrogels with tunable physical properties were then synthesized by mixing different ratios of GelMA and MeTro. Tropoelastin is a precursor to elastin, a highly stretchable, positively charged protein that provides pliability to elastic tissues. Gelatin constitutes a denatured form of collagen, which is the main structural protein found in bone, cartilage, skin, and tendons. Both gelatin and tropoelastin can be similarly functionalized through methacrylation to form photocrosslinkable precursors, and then blended together to form GelMA/MeTro composite hydrogel upon exposure to light, as shown in FIG. 1C. GelMA/MeTro hydrogels were formed by using different ratios of GelMA/MeTro (i.e., 0/100, 20/80, 50/50, 80/20, and 100/0), total polymer concentrations (i.e., 5%, 10%, and 15% (w/v)), and exposure times (i.e., 30, 60, 180, and 360 s).

Figure 1E:
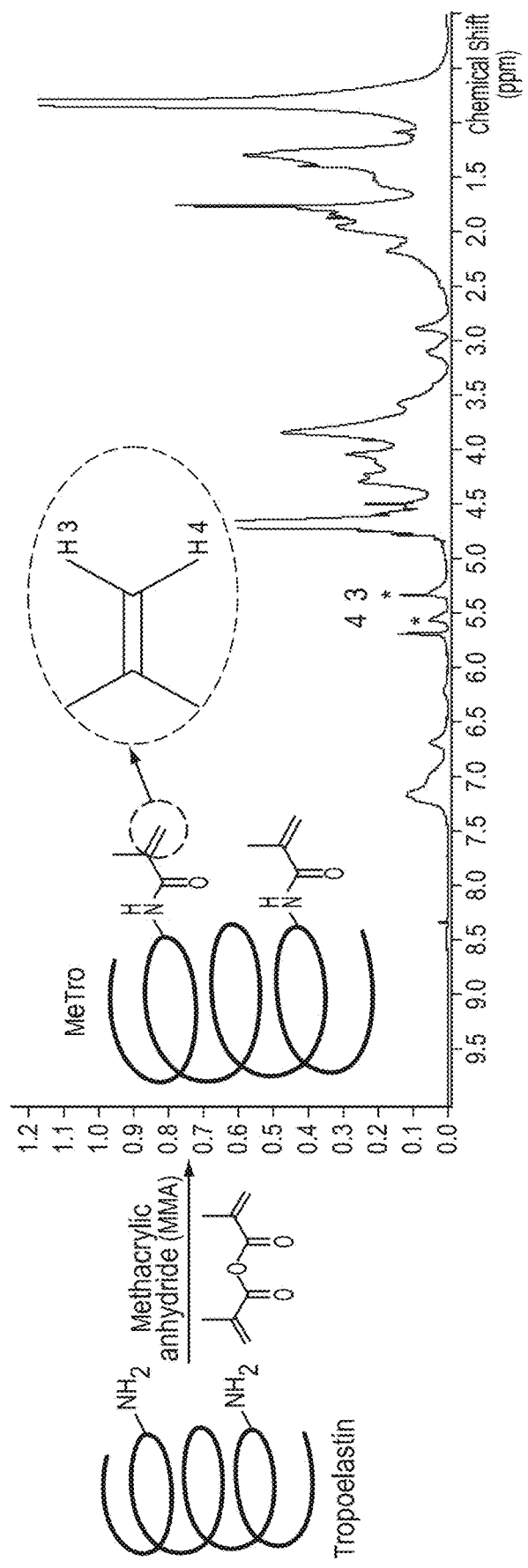
FIG. 1E depicts the methacrylol substitution of tropoelastin to form MeTro, confirmed using $^1$H NMR, the $^1$H NMR sprectra shown on the right-hand side.
Figure 1F:
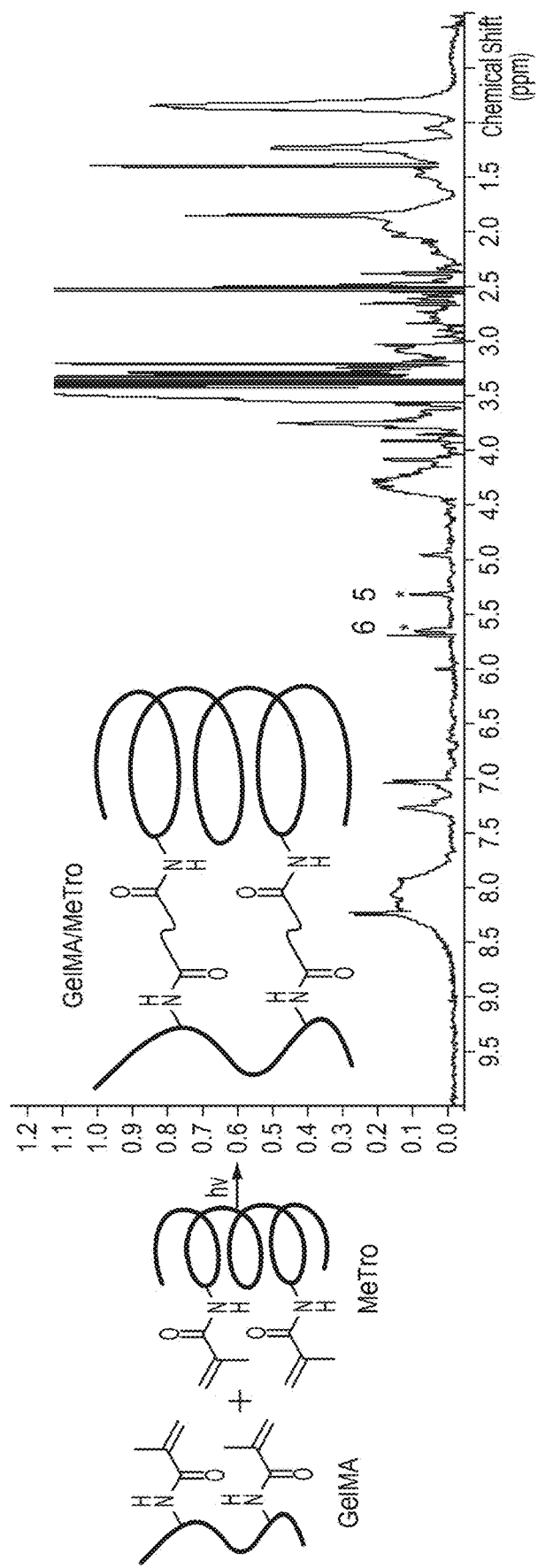
FIG. 1F depicts GelMA/MeTro composite preparation and the $^1$H NMR spectra of the composite partially dissolved in DMSO-d6 on the right-hand side.

Validation and quantification of the degree crosslinking within the composites were carried out by 1H NMR (500 MHz) analysis. $^1$H NMR spectra were taken from dissolved GelMA (FIG. 1D) and MeTro (FIG. 1E) in deuterium oxide (D20), and partially dissolved GelMA/MeTro composite in deuterated dimethyl sulfoxide (DMSO-d6) (FIG. 1F). These results indicated that the methacrylate groups present in GelMA and MeTro were involved in the formation of the composite hydrogel. In these spectra, the methacrylate groups ($-C=CH2$) appeared as characteristic peaks at $\delta=5.3$ ppm (peak 1, 3, 5) and $\delta=5.7$ ppm (peak 2, 4, 6). The relative change in these peaks normalized to phenol conjugated peaks indicated that the degree of crosslinking within the composite was approximately 73.3%.

2.2 Mechanical Characterization of GelMA/MeTro Hydrogel

The mechanical properties of GelMA/MeTro hydrogels can be tuned by varying the ratio of GelMA to MeTro (FIGS. 2A-F), the total polymer concentration (FIGS. 3A and 3B), and the crosslinking time (FIGS. 3C and 3D). Tensile tests showed statistically significant differences in the mechanical properties between the composites, and pure GelMA and MeTro hydrogels (FIGS. 2A-C). The results demonstrated that the tensile modulus of the engineered composites decreased consistently by increasing the GelMA/MeTro ratio (FIG. 2A). In addition, the elastic moduli of the composites were reduced from 49.92±4.91 kPa for pure MeTro to 14.45±3.32 kPa for 50/50 GelMA/MeTro (FIG. 2A). The strain at failure or extensibility decreased with increasing GelMA concentrations (from 148.2±24.3% for pure MeTro to 69.0±10.1% for 50/50 GelMA/MeTro) (FIG. 2B). The ultimate stress was reduced significantly from 79.10±14.76 kPa for pure MeTro to 12.47±3.19 kPa for 50/50 GelMA/MeTro hydrogels, with no significant differences among other composite formulations (FIG. 2C).

Based on the cyclic compression tests, the composites exhibited compressive moduli greater than those of pure GelMA or MeTro hydrogels (FIGS. 2D-E). The compressive modulus of GelMA/MeTro hydrogel were shown to increase from 14.96±4.04 kPa for pure GelMA and 9.25±1.63 kPa for pure MeTro hydrogels, to a maximum of 35.90±6.13 kPa for 50/50 GelMA/MeTro hydrogels (FIG. 2E). Cyclic compressive testing revealed that increasing the concentration of GelMA decreased the amount of energy loss in the composite hydrogels (from 37.13±0.10 kJ for pure MeTro, down to 21.46±3.02 kJ for pure GelMA) (FIG. 2F). The results also demonstrated that the compressive moduli of 50/50 GelMA/MeTro hydrogels increased concomitantly by increasing the total polymer concentration (FIGS. 3A and 3B). We also investigated the effect of light exposure time on the compressive modulus of 50/50 GelMA/MeTro hydrogels formed at 10% total polymer concentration (FIGS. 3C and 3D). These results showed that the compressive moduli of the composites increased from 4.48±0.94 kPa for 30 s exposure time, to 52.50±10.77 kPa for 360 s exposure time (FIGS. 3C and 3D). Taken together, these results suggest that GelMA/MeTro hydrogels may be able to withstand the loading and unloading conditions to which nerves are exposed to under physiological settings.

2.3 Pore Characteristics, Swelling Ratios, and In Vitro Degradation of GelMA/MeTro Hydrogels Scanning electron microscopy (SEM) analyses demonstrated the influence of varying ratios of GelMA and MeTro, as well as the total polymer concentration on the relative pore sizes of the composites (FIGS. 4A and 4B). Although changes in hydrogel pore sizes among different composite formulations were identified, the process of lyophilization prior to SEM analysis can also alter the porosity. However, GelMA/MeTro hydrogels were all processed in the same conditions, based on a method reported previously in the literature (Y. C. Chen, R. Z. Lin, H. Qi, Y. Yang, H. Bae, J. M. Melero-Martin, A. Khademhosseini, *Adv Funct Mater*

2012, 22, 2027). Therefore, any differences in apparent porosity should be due to changes in the hydrogel composition. Our results demonstrated that the average pore sizes increased from 21.08±12.06 μm for pure MeTro, to 31.81±11.05 μm for 50/50 GelMA/MeTro, and to 46.78±8.73 μm for pure GelMA (FIG. 4B).

The swellability of the composite hydrogels was also dependent on the GelMA/MeTro ratio (FIG. 2G), as well as the total polymer concentration (FIG. 5A) and crosslinking time (FIG. 5B). The swelling ratio of pure GelMA hydrogels was nearly five times that of MeTro after 24 h of incubation in Dulbecco's phosphate buffered saline (DPBS), while the composite hydrogels with 20/80, 50/50, and 80/20 GelMA/MeTro ratios exhibited 184.87±24.40%, 416.52±31.79%, and 650.07±31.84% swelling ratios (FIG. 2G). For pure MeTro and all of the composites tested, the maximum swelling ratio was reached after 2 h, whereas GelMA hydrogels continued to swell throughout the experiment (24 h) (FIG. 2G). In addition, it was found that the swelling ratios for all tested GelMA/MeTro composites decreased by increasing the total polymer concentrations (FIG. 5A). Similarly, we found that increasing the time of crosslinking also resulted in a decrease in swelling ratio, due to the increased degree of crosslinking (FIG. 5B).

The high-water content of hydrogels makes them suitable for tissue engineering applications, by providing a highly permeable environment for the diffusion of nutrients, oxygen, and metabolic waste. Depending upon the target tissue, the swelling ratios of the composites can be tuned to match the characteristics of the native tissue. Alternatively, materials that exhibit limited swelling may be favorable as surgical adhesives for nerve repair as high levels of swelling may increase interstitial pressure at the injury site (see Z. Z. Khaing et al. *Cells Tissues Organs* 2016, 202, 67; and A. R. Nectow et al. *Tissue Eng Part B Rev* 2012, 18, 40). Therefore, the ability to fine-tune the swellability of GelMA/MeTro hydrogels allows adaptations to the formulation of this biomaterial for PNI repair.

Previous studies have shown that swellability may also influence the rate of degradation for hydrogels in vitro (see J. Lam et al. *J Biomed Mater Res A* 2014, 102, 3477). Our results demonstrated that increasing the concentration of GelMA in the composites led to an increase in the degradation rate in DPBS supplemented with 5% fetal bovine serum (FBS) over 14 days (FIG. 2H). The degradation ratio of the composites increased from 3.85±3.55% for pure MeTro to 18.73±3.88% for pure GelMA after 24 h (FIG. 2H). Interestingly, there was no significant difference between the degradation of the 50/50 GelMA/MeTro (5.48±4.78%) composite and that of pure MeTro. Previous studies have demonstrated that complete degradation of GelMA- and MeTro-based hydrogels in vitro could not be achieved without the addition of collagenase, or elastase enzymes. GelMA hydrogels contain several matrix metalloproteinase (MMP)-sensitive degradation sequences (see J. Vandooren et al. *Crit Rev Biochem Mol Biol* 2013, 48, 222), which can result in rapid degradation rates in vivo (see Y.C. Chen et al. *Adv Funct Mater* 2012, 22, 2027). Previous works have demonstrated that SCs overexpress MMPs to remove cellular debris following PNI (see H. Liu et al. *J Neuropathol Exp Neurol* 2010, 69, 386). Therefore, the combination of GelMA with MeTro may reduce the degradation rate of the composites and enhance their potential to be used for peripheral nerve repair in vivo. Taken together, the results demonstrated that GelMA/MeTro composites can be tuned to exhibit suitable stiffness, swelling capacity, and degradation rates for different neural tissue engineering applications.

2.4 Adhesion Strength of GelMA/MeTro Composite for Nerve Anastomosis

[1] The use of nylon or polypropylene sutures for nerve anastomosis has been associated with increased tension, inflammation, and the development of FBR (see L. M. Wolford et al. *Proc (Bayl Univ Med Cent)* 2003, 16, 152; S. Kehoe et al. *Injury* 2012, 43, 553; and T. H. Chuang et al. *Tissue Eng Part C Methods* 2013, 19, 427). A composite hydrogel with high adhesion to native neural tissue was engineered, which can be used to reduce the number of sutures needed for nerve reconstruction (FIG. 6A). Ex vivo adhesion tests on adult rat sciatic nerves, reconnected using GelMA/MeTro hydrogels, demonstrated a rapid and improved mechanical stabilization of severed tissue over fibrin-based alternatives (FIG. 6B). For adhesion tests, a 50/50 GelMA/MeTro formulation at 10% total polymer concentration was used. The results indicated that GelMA/MeTro composites with an adhesive strength of 165.2±25.8 kPa were able to significantly outperform Evicel® (10.3±3.4 kPa) when used for nerve anastomosis (FIG. 6B). In addition, the adhesive strength of GelMA/MeTro composites was 2-fold higher than a previously proposed photocrosslinkable chitosan hydrogel for nerve repair (see T. Rickett et al. *Int Conf Biomed* 2009, DOI: 10.1109/BMEI.2009.53054601078). The strain at failure for ex vivo anastomosis was 14±3% (FIG. 6C), which was higher than the value reported for the permanent nerve dysfunction (~10% strain). Therefore, GelMA/MeTro adhesives should be capable of withstanding the physiological levels of strain for immobilized extremities following PNI, which is common for the treatment of musculoskeletal injuries. Histological assessment of the interface between the composites and the native nerve tissue showed penetration and entanglement of GelMA/MeTro adhesives at the interface of an anastomosed sciatic nerve (FIG. 6D). In addition, the bonding strength of photocrosslinked adhesives used in vivo could be further increased by covalent bonds generated by free radicals during the curing process (see M. Yao et al. *Lasers Surg Med* 2010, 42, 123). Similarly, covalent bonding is also likely to occur due to hydrogen and amine bonding, owing to the presence of free hydroxyl groups in the polymers (see J. D. Smart, *Adv Drug Deliv Rev* 2005, 57, 1556; and M. Mehdizadeh and J. Yang, *Macromol Biosci* 2013, 13, 271.) The high adhesion of the hydrogel to the tissue can be also due to tissue/adhesive interlocking. The mechanism by which adhesive materials and tissue collagen fibers interlock at the interface has been previously reported (see Lang N, Pereira M J, Lee Y, et al. A blood-resistant surgical glue for minimally invasive repair of vessels and heart defects. Sci Transl Med 2014; 6:218ra6). In addition to this physical interlocking, the charge interactions (positively charged tropoelastin, negatively charged glycosaminoglycans) could further improve the adhesive strength of the hydrogel to the tissue (see Tu Y, Weiss A S. Transient tropoelastin nanoparticles are early-stage intermediates in the coacervation of human tropoelastin whose aggregation is facilitated by heparan sulfate and heparin decasaccharides. Matrix biology 2010; 29:152-9; and http://stm.sciencemag.org/content/9/410/eaai7466).

2.5 3D Encapsulation of SCs in GelMA/MeTro Composite Hydrogels

The potential of GelMA/MeTro hydrogels to be used for 3D encapsulation of SCs was investigated. SCs were encapsulated in 80/20 GelMA/MeTro hydrogels at 10% (w/v) total polymer concentration. This formulation was selected as it exhibited moduli closest to the optimal matrix stiffness previously reported for SC growth (~7.45 kPa), while still providing adequate elasticity and stability. Both gelatin and tropoelastin are likely to promote SC adhesion because of cell-binding domains within their structure. Cell viability, proliferation, metabolic activity, and phenotype maintenance of 3D encapsulated SCs in vitro was evaluated. The results showed that SC viability increased from 58.85±3.79% on day 1, to >85% by day 5 post-encapsulation (FIGS. 7A and 7B). Initial reduction of cell viability may be explained due to a combination of the toxicity induced by the free radical initiator, and UV light exposure. In particular, UV light has previously been shown to promote the activation of the pro-apoptotic transforming growth factor δ(TGF-δ). SC viability was then increased due to the removal of the free radical initiator after replacement of culture medium, and the proliferating ability of SCs. Instead of free radical initiator and UV light exposure, visible light-activated photoinitiators such as Eosin Y or lithium phenyl-2,4,6-trimethylbenzoylphosphinate (LAP) can be used, to circumvent this limitation. Cell proliferation and spreading within the hydrogels were also confirmed by fluorescent staining of F-actin/4',6-diamidino-2-phenylindole (DAPI) at days 1, 3, and 5 post-encapsulation. SCs exhibited round morphologies with little spreading at day 1 post encapsulation, followed by proliferation and spreading within the matrix at day 5 (FIG. 7C). These results were further confirmed by quantitative evaluation of cell proliferation, by counting the number of DAPI-stained cell nuclei over time (FIG. 7D). The expression of S100, a SC specific marker, also confirmed that the SC phenotype was maintained in the described composites (FIG. 7E) (see Z. Liu et al. *PLoS One* 2015, 10, e0123278). Furthermore, the Prestoblue assay demonstrated that the metabolic activity of the encapsulated SC increased consistently throughout the 5 days of culture (FIG. 7F). Interestingly, both the metabolic activity and number of cells remained the same for days 1 and 3, due to the initial quiescent behavior following encapsulation. However, the increase in cell number and metabolic activity at day 5 demonstrated that the composite hydrogels can support the adhesion, proliferation, and spreading of 3D encapsulated SCs in vitro.

3D encapsulated SCs in GelMA/MeTro hydrogels displayed a characteristic elongated morphology. In contrast, alginate-based materials used previously for 3D encapsulation of SCs have previously been reported to have led to round morphologies, which are associated with atypical growth. Our results demonstrated that GelMA/MeTro hydrogels exhibited high cytocompatibility in vitro, which is essential for the delivery of SCs for PNI repair in vivo.

Figure 8C:
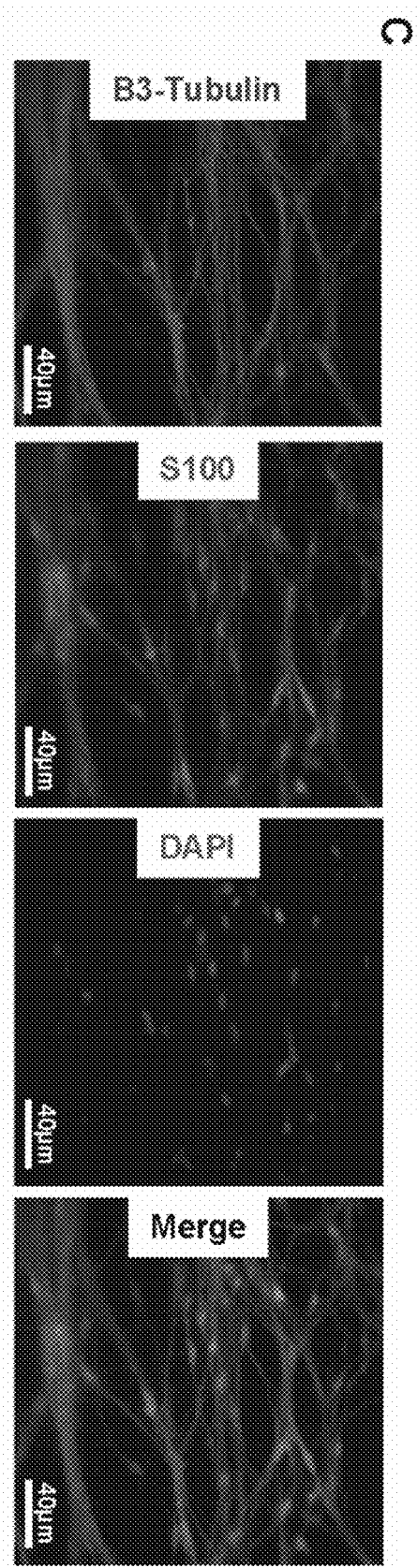
FIG. 8C provides representative high magnification immnocytofluorescent images of axonal extension, β-3-tubulin, and Schwann cell morphology, S100 (red), and cell nuclei (cyan) (ns: $p>0.05$, $****p<0.0001$).

2.6 Dorsal Root Ganglia (DRG) Outgrowth within GelMA/MeTro Composite Hydrogel DRGs were encapsulated within GelMA, MeTro, and 50/50 GelMA/MeTro (10% total polymer concentration) composite to examine the degree to which neurites extend though the hydrogels. The 50/50 GelMA/MeTro formulation was selected for these experiments, since there were no significant differences in the degradation rate of the composite throughout the experiment, when compared to pure MeTro hydrogels (FIG. 2H). As shown in FIG. 8A, robust neurite outgrowth was observed within pure GelMA hydrogels and GelMA/MeTro composites. In contrast, neurite outgrowth was hindered in pure MeTro hydrogels. However, even though GelMA exhibited lower stiffness compared to MeTro, pure GelMA hydrogels would degrade to rapidly to be used in vivo for this application (see Y. C. Chen et al. *Adv Funct Mater* 2012, 22, 2027; and J. Vandooren et al. *Crit Rev Biochem Mol Biol* 2013, 48, 222). Interestingly, despite the difference in mechanical stiffness, the quantification of neurite outgrowth (see S. Park et al. *Sci Rep* 2015, 5, 9669) revealed no statically significant differences between GelMA (0.49±0.08 mm$^2$) and composite hydrogels (0.50±0.09 mm$^2$)(FIG. 8B). High magnification images of neurite outgrowth suggested a cooperative migratory mechanism with SCs within GelMA/MeTro hydrogels (FIG. 8C), which may help maintain neuron viability and facilitate nerve growth. Taken together, the results suggest that GelMA/MeTro composites can be used as a nerve glue for anastomosis or as a filler for nerve conduits to increase the rate of axonal regeneration.

2.7 Subcutaneous Implantation and In Vivo Degradation of GelMA/MeTro Hydrogel The PNS has a remarkable regenerative potential when compared to the central nervous system in vivo. However, this regenerative ability is insufficient for large gap injuries (>4 cm), since the axonal growth rate has been shown to be approximately 1 mm/day. This limitation must be taken into consideration for the design of biomaterials to be used for the treatment of PNIs. Successful regeneration requires these materials to support outgrowing axons traversing the coaptation site. Degradation of fibrin-based materials occurs within a 2-3 week period. Furthermore, this characteristic may be sub-optimal for patients in which regeneration may take longer than the average such as senior or diabetic patients. Thus, a biomaterial with tunable and comparatively longer degradation rates could be used to improve therapeutic efficacy. A murine subcutaneous implantation model was used to evaluate the degradation of the composite hydrogels in vivo. For this, we used a 50/50 GelMA/MeTro formulation (10% total polymer concentration, 180 s crosslinking). As shown in FIG. 9A, visual inspection of the explanted samples revealed that the size of GelMA/MeTro hydrogels decreased consistently until day 28, followed by complete biodegradation at day 56. This observation was further confirmed by quantitative analysis of the degradation ratios, as determined by changes in both weight and volume (FIG. 9B). The results showed that, by day 28 post-implantation, 68.8±25.9% (by weight) and 32.1±20.2% (by volume) of the composites still remained. These discrepancies between the estimations by weight and by volume are likely due to the progressive tissue ingrowth within the composites (FIGS. 9C-E). The slower degradation rate of GelMA/MeTro composites compared to fibrin-based materials (~8 weeks vs. 2-3 weeks) may provide a suitable microenvironment by protecting the healing site from fibrosis and inflammation.

As shown in FIGS. 9C-E, histological examination of explanted samples at days 4 to 28 post-implantation revealed minimal host immune responses and progressive tissue ingrowth. This observation was further confirmed by immunohistofluorescence staining against surface markers representative of pro-inflammatory cell types (FIGS. 9F-K) Fluorescent images showed no T-lymphocytes (CD3) (FIG. 9F) and mild macrophage (CD68) infiltration around the implant (FIG. 9I), at day 4 post-implantation. Moreover, the results also showed that there was no sustained inflammatory response, as demonstrated by the absence of immune cells at day 28 post-implantation (FIGS. 9H and 9K). Microscopic and histological examination of subcutaneously implanted samples revealed significant ingrowth of predominantly non-inflammatory tissue. Furthermore, GelMA/MeTro hydrogels were shown to elicit minimal immunogenicity, and to be completely biodegraded at day 56 post-implantation, which is a clinically relevant time frame for PNI recovery. Taken together, these results demonstrated the remarkable in vivo biocompatibility of GelMA/MeTro hydrogels.

3. CONCLUSION

GelMA/MeTro composites exhibited higher adhesive strength to neural tissues, when compared to clinically used fibrin-based adhesives. In addition, GelMA/MeTro hydrogels supported the proliferation and spreading of 3D encapsulated SCs in vitro. The results also indicated that 3D encapsulated SCs maintained their phenotype, as shown by immunofluorescent staining against the S100 marker. GelMA/MeTro composites provided a supportive microenvironment for neurite extension, as demonstrated by the robust neurite outgrowth of encapsulated DRGs. The composites were shown to be biocompatible and biodegradable, as confirmed by subcutaneous implantation in a murine animal model. Taken together, these results support the use of GelMA/MeTro hydrogels for regenerative nerve tissue engineering applications for the treatment of PNI.

4. Experimental Section

MeTro synthesis. Human tropoelastin isoform SHELΔ26A (synthetic human elastin without amino acid residues 27-724 of GenBank entry AAC98394) was produced and purified from recombinant *Escherichia coli* (see N. Annabi et al. *Biomaterials* 2013, 34, 5496). The tropoelastin isoform was then methacrylated as described previously by Annabi et al. (see N. Annabi et al. *Biomaterials* 2013, 34, 5496). Briefly, 8% (v/v) methacrylic anhydride (MA, Sigma) was added to a 10% (w/v) tropoelastin solution in DPBS (Sigma). The reaction was carried out for 12 h at 4° C. and then stopped by adding a 3× dilution of cold (4° C.) DPBS. The diluted solution was then dialyzed (Slide-A-Lyzer Dialysis Cassette, 3,500 MWCO) for 48 h in distilled water at 4° C. The resulting MeTro was frozen at −80° C., lyophilized, and stored at room temperature for on demand use.

GelMA synthesis. GelMA was made by adding 8% (v/v) MA to a 10% (w/v) fish gelatin solution in DPBS dropwise, as previously described (see J. W. Nichol et al., *Biomaterials* 2010, 31, 5536). The reaction was carried out at 60° C. for 2 h, and stopped by adding a 3× dilution of warm (60° C.) DPBS. The mixture was dialyzed (Spectra/Por 12-14 kD, Fisher Scientific) using distilled water for 1 week at 60° C., frozen at −80° C., lyophilized, and stored at room temperature for use on demand.

Hydrogel fabrication. Composite hydrogels were synthesized by using varying ratios of GelMA and MeTro (0/100, 20/80, 50/50, 80/20, 100/0 GelMA/MeTro) following the proposed chemistry in FIG. 1. In addition, hydrogels were fabricated by using three different total polymer concentrations (5%, 10%, and 15% (w/v)) at a fixed 50/50 GelMA/MeTro ratio. For each condition, hydrogel precursor solution was prepared in distilled water with 0.5% (w/v) 2-hydroxy-1-(4-(hydroxyethoxy) phenyl)-2-methyl-1-propanone (Irgacure 2959, CIBA Chemicals) as a photoinitiator on ice. Hydrogel precursors were then photocrosslinked by exposing to 6.9 mW/cm$^2$ of UV light (320-390 nm) for 180 s for all material characterizations and 35 s for the in vitro cell studies.

$^1$HNMR characterization. A Varian Inova-500 $^1$H NMR spectrometer was used to determine the degree of crosslinking within the GelMA/MeTro composite hydrogels. Spectra, as shown in FIG. 1, were acquired for uncrosslinked GelMA and MeTro dissolved in D2O, and the supernatant from a partially dissolved composite (50/50 GelMA/MeTro, 10% (w/v) total polymer concentration, 180 s crosslinking) kept in DMSO-d6 (Sigma) overnight at room temperature. The peaks at δ=5.3 ppm and δ=5.7 ppm indicate the presence of methacrylate groups. The degree of crosslinking was calculated by the reduction in these peaks as compared to both GelMA and MeTro using the following equation: Degree of Crosslinking (%)=(PAb−PAa)/PAb*100. Where $PA_b$ is equal to the peak area before crosslinking and $PA_a$ is the peak area after crosslinking. Peak areas were measured using ACD/Spectrus NMR to integrate the area of the curve with respect to phenyl conjugated peaks at δ=6.5-7.5 ppm.

Mechanical characterization. The compressive and tensile properties of hydrogel formulations were examined using a universal load frame (Instron Model 5542) with a 10 N load cell. Hydrogel samples were prepared in custom polydimethylsiloxane (PDMS, Sylgard) molds (cylinders of 6.30 mm diameter by 1.50 mm depth for compressive testing; and cuboids of 12.40 mm length, 5.00 mm width, 0.80 mm depth for tensile testing). The hydrogels were prepared as described above (section 2.3) and allowed to swell in DPBS for 2 h at 37° C. prior to mechanical testing.

For compression tests, hydrogels were loaded between two compression plates and cyclic uniaxial compression tests were conducted at a 1 mm/min strain rate (10 cycles). Compression displacement and load for each cycle were recorded using Bluehill software.

Compressive modulus was calculated as the tangent slope of the linear region of the stress-strain curves between 0.1-0.25 stain level. The area between the loading and unloading curves for cycle 8 was calculated as the energy loss.

To test tensile properties, hydrogels were mounted between double sided tape within tensile grips, and pulled at a 1 mm/min strain rate until failure. Elastic modulus was identified from a fit of the linear portion of the stress-strain curve. The ultimate stress and extensibility were measured as the stress, and the maximum strain/extensibility at failure, respectively. The effect of GelMA/MeTro ratio, total polymer concentrations, and light exposure time on the mechanical properties of the engineered hydrogels were investigated, where at least three samples were prepared for each set of conditions and the average and standard deviations were obtained.

Swelling ratio characterization. Hydrogels were prepared from different GelMA/MeTro ratios (100/0, 80/20, 50/50, 20/80 and 0/100), as well as different total polymer concentrations (10%, 15%, and 20% (w/v)) and varying crosslinking times (30, 60, 180, and 360 s) in cylindrical molds used for compression test. Hydrogel samples were frozen at −80° C., lyophilized, and weighed to determine their dry weights. The samples were then soaked in DPBS at 37° C. for different time points (1, 2, 4, 8, 12, 24 h) and re-weighed. Swelling ratios were calculated as the change between the wet and dry weights over the dry weight. At least three samples were prepared for each set of conditions and the average and standard deviations were obtained.

SEM analysis. Composite hydrogels were prepared from a range of GelMA/MeTro ratios (100/0, 80/20, 50/50, 20/80 and 0/100) at 10% (w/v) total polymer concentration. The samples were lyophilized and mounted on aluminum pin stubs. All samples were sputter coated with a 6 nm gold/palladium (Au/Pd) layer. SEM images were acquired by using a Hitachi S-4800 SEM at 15 kV and an 8 mm working distance. At least three samples for each type of condition were used for SEM analysis. Three images were obtained per sample and at least 15 pores were measured to obtain the average pore sizes for each condition using NIH ImageJ software.

In vitro degradation studies. Composite hydrogels were prepared as described above (section 2.5). Samples were frozen at −80° C. overnight, lyophilized for 24 h, and their dry weights were measured. Each sample was kept in 1 ml of 5% FBS (Corning) in DPBS at 37° C. for 2 weeks. At established time points of 1, 7 and 14 days, the solutions were removed and the samples were frozen, lyophilized, and weighed again. The percentage of degradation was calculated as a ratio of the final and initial dry weights of the hydrogels. At least three samples were measured at each time point.

Adhesive strength of MeTro/GelMA hydrogel for nerve anastoinosis. The efficacy of GelMA/MeTro composites as a nerve glue was examined ex vivo. Adult male Wistar (200-250 grams) and adult female Sprague-Dawley (250-350 grams) rats were treated following Northeastern University's Institutional Animal Care and Use Committee (IACAUC) approved protocols. Sciatic nerves were extracted from both legs, and stored in Hibemate®-A on ice for 4-12 h prior to transection and adhesion testing.

On a Teflon® surface, each nerve was attached with super glue between two pieces of 150 grit sandpaper with ~12 mm gauge length. Using titanium clamps, nerves were then secured in a Bose Electroforce 3200-ES with a 1000-gram load cell. Nerve trunks were transected with surgical scissors and reconnected via the application of ~5 µL of 50/50 GelMA/MeTro precursor solution at 10% total polymer concentration and direct exposure to UV light for 180 s. Transected nerve controls were also reconnected with ~5 µL Evicel®, a commercially available fibrin-based adhesive. Approximately 500 µL of Hanks' Balanced Salt Solution was carefully pipetted onto the nerve to rehydrate both the nerve and hydrogel before being pulled at a rate of 0.08 mm/sec until failure. The load and displacement data were recorded at 20 Hz. Each hydrated nerve was imaged and analyzed by ImageJ to measure its diameter to determine the cross-sectional area prior to testing. For each material type, a total of six nerves were used. The adhesion strength was measured as the stress at failure.

To observe the adhesive-tissue interface, the nerves anastomosed by the engineered adhesives were fixed in 4% paraformaldehyde (Sigma) for 4 h, kept overnight in 30% sucrose at 4° C., then embedded in Optimal Cutting Temperature (OCT) and flash frozen. The fixed samples were then cryo-sectioned (15 µm slices) using a Leica Biosystems CM3050S Research Cryostat and H&E (Sigma) staining was performed to observe adhesive/tissue interface.

Primary SC isolation and culture. Primary SCs were isolated from day two old (p2) Sprague-Dawley neonatal rat (Charles River) sciatic nerves (see A. N. Koppes et al. *Tissue Eng Part A* 2014, 20, 494), following a protocol approved by IACAUC. The sciatic nerves were harvested and kept in complete culture medium (Dulbecco's Modified Eagle Medium (DMEM, Corning) supplemented with 10% FBS, 2 mM L-glutamine (L-glut, Gibco), and 50 U mL$^{-1}$ penicillin/streptomycin (P/S, Gibco)) on ice for a maximum of 4 h. Dissected nerves were minced into 1-2 mm pieces under sterile conditions and left to incubate in a 6-well plate using complete culture medium in standard conditions (37° C., 5% $CO_2$). Tissues were transferred to a new dish after visual confirmation of fibroblast migration. Three-four days after SC migration, cells were cultured with complete medium supplemented with $10^{-5}$ M cytosine arabinoside (ARA-C, Sigma) for 72 h to remove contributions from the highly mitotic fibroblasts. Next, a complement-mediated cell lysis was used to eliminate remaining fibroblasts. Cells were detached with 0.25% trypsin/EDTA (Corning) and pelleted at 200 g for 5 min. Fibroblasts were targeted by re-suspending in 1 mL anti-CD90/Thy 1.1 (diluted 1:500 v/v in DMEM, Cedar Lane Labs) and incubated under standard conditions for 30 min. Treated cells were pelleted, re-suspended in 1 mL rabbit complement, and incubated for 30 mm with standard conditions to selectively lyse the fibroblasts. After incubation, cells were centrifuged down, re-suspended in SC maintenance medium (complete medium supplemented with 6.6 mM forskolin (Sigma) and 10 µg mL$^{-1}$ bovine pituitary extract (Corning)), and cultured in a flask for expansion. Lysis was repeated if fibroblast impurities remain. SC purity was assessed using anti S-100 (DAKO). Maintenance medium was changed every other day and SCs were passaged before 100% confluency until P10.

3D encapsulation of SCs. Cells were mixed with the hydrogel precursor solution containing 80/20 GelMA/MeTro (10% total polymer concentration) at a density of 5×10$^6$ cells/mL. Approximately 7 µL cell-laden gel precursor solution was placed between a 150 µm-tall spacer and a 3-(trimethoxysilyl) propyl methacrylate (TMSPMA, ACROS Organics) coated glass slide, followed by exposure to light for 35 s to form photocrosslinked cell-laden GelMA/MeTro hydrogels. The cell-laden hydrogels were washed three times with warmed (37° C.) non-supplemented DMEM to remove any unreacted precursor before being transferred into a 24-well plate with 400 µL of SC maintenance medium. Samples were incubated for 1, 3, and 5 days in standard culture conditions, and medium was changed every other day. Cellular viability and proliferation, and immunocytochemistry assays were preformed 1, 3, and 5 days post-encapsulation. SC viability was determined via a LIVE/DEAD® viability/cytotoxicity kit (Life Technologies) per instructions from the manufacturer. Live (green) and dead (red) cells then were imaged by using an inverted fluorescence microscope (Zeiss Axio Observer Z1). Cell viability was calculated by counting the number of the live cells divided by total cell number using ImageJ software. At least three samples were prepared for each measurement and the average and standard deviations were obtained from at least four images per sample. The metabolic activity of SCs was evaluated using the PrestoBlue assay (Life Technologies). Prior to measuring the fluorescence on days 1, 3, and 5, SC-laden hydrogels were incubated in 400 µL complete medium with 10% PrestoBlue reagent for 1 h at 37° C. The resulting fluorescence was measured (excitation 535-560 nm; emission 590-615 nm) using a Synergy HT fluorescence plate reader (BioTek). At least four samples were used to measure the metabolic activity and the average and standard deviation were calculated for each time point.

Whole DRG isolation. To determine the extent neurite extension that occurs within the engineered hydrogels, DRGs were utilized to represent a population of PNS neurons. DRGs were isolated from p2 Sprague-Dawley neonatal rats, with IACAUC approval. The spinal column was removed and the vertebral bodies were transected to expose the spinal cord and excise individual DRGs from the lumbar and thoracic regions. Nerve roots and connective tissue were trimmed away and then each cleaned DRG was stored in Hibernate®-A on ice for less than 24 h prior to use (see A. N. Koppes et al. *Acta Biomater* 2016, 39, 34). DRGs were collected and randomized across three animals from two separate litters (total=six p2 pups) for all experiments.

3D encapsulation and culture of DRG. A single DRG was encapsulated in hydrogels in a similar manner to SCs (see section 2.10.2). Samples were photocrosslinked by exposure to light for 35 s and washed thrice with warmed (37° C.), non-supplemented Neurobasal medium (Gibco) to remove any unreacted material before being transferred into a 24-well plate with 400 µL of DRG maintenance medium (Neurobasal supplemented with 1× B27 (Gibco), 2 mM L-glut, 50 U mL$^{-1}$ P/S, and 25 ng mL$^{-1}$ nerve growth factor (Gibco)). Samples were incubated for 7 days in standard culture conditions, and medium was changed every other day.

Immunocytochemistry (Actin/DAPI/S100/β3T). Morphological properties of encapsulated SCs were investigated by staining cell-laden hydrogels with corresponding cell and structural protein markers for both SCs and PNS neurons. Samples were fixed in 4% paraformaldehyde for 30 min, permeabilized with 0.1% X-100 Triton (Sigma) for 30 min at room temperature, and blocked overnight at 4° C. with 5% goat serum (Sigma). After blocking, rabbit anti S-100 (DAKO) and/or mouse anti β-3 tubulin (Invitrogen) (1:400 in 5% goat serum) were added overnight at 4° C. After primary antibody incubation, cell-laden hydrogels were washed three times with DPBS to remove any unbound primary antibody. Next, anti-rabbit and/or anti-mouse secondary antibody (1:200 and phalloidin (Life Technologies) 1:400 in goat serum) were added overnight at 4° C. Samples were washed five times with DPBS with 15 min intervals and mounted on cover slides with ProLong® Gold Antifade with DAPI before imaging using an inverted fluorescence microscope (Zeiss Axio Observer Z1).

Image Analysis for Neurite Outgrowth. DRG total outgrowth area was calculated using a custom MATLAB algorithm (see S. Park et al. *Sci Rep* 2015, 5, 9669). The DRG center was user selected and 360 equally distributed radial lines were draw centered on this point. Using a cutoff of 1σ standard deviation above the average pixel intensity values, the two end points on each radial line were identified. The total outgrowth area was then calculated as the area within the 2D outline of all end points (720, two per line). A minimum of three hydrogels were analyzed and the average and standard deviations were obtained.

Subcutaneous implantation of GelMA/MeTro hydrogels to assess in vivo degradation and biocompatibility. Male Wistar rats (200-250 grams) (Charles River) were anesthetized using 1-2.5% isoflurane, followed by 0.02 to 0.05 mg/kg subcutaneous buprenorphine administration. Back fur was shaved and the skin was scrubbed with chlorhexidine. Four 1 cm lateral subcutaneous pockets were prepared on each side of the medio-dorsal skin using a scalpel. 50/50 GelMA/MeTro (10% total polymer concentration, 180 s crosslinking) composites were prepared in cylindrical models (4.92 mm diameter, 3.85 mm height) under sterile conditions and were then frozen at −80° C. overnight, lyophilized for 24 h, weighed, and measured. Sterile and lyophilized hydrogels were introduced into the pockets, away from the opening, and incisions were closed using 3-0 polypropylene sutures. On days 4, 14, 28, and 56 post-implantation, rats were euthanized and the hydrogels along with the adjacent tissue were explanted. Separate samples were used for H&E staining, immunohistochemistry, and biodegradation analyses. To determine the percentage of degradation, the adjacent tissue was carefully removed from the sample before being frozen, lyophilized, and weighed. Degradation ratios were reported as Final Weight/Initial Weight for each post implantation time point. At least three samples were used to report the average and standard deviation of each time point.

Following explanation, samples were fixed for 4 h in 4% paraformaldehyde, incubated overnight at 4° C. in 30% sucrose, then embedded in OCT compound, and flash frozen in dry ice. Fifteen-µm cryo-sections were obtained using a Leica Biosystems CM3050S Research Cryostat. Cryo-sections were attached to positively charged slides and mounted using DPX mounting medium (Sigma). Slides were processed for H&E per instructions from the manufacturer. Immunohistological staining was performed on mounted cryo-sections as previously reported (see N. Annabi et al. *Adv Mater* 2016, 28, 40). Samples were stained for lymphocytes (Anti-CD3 [SP7], ab16669, Abcam) and macrophages (anti-CD68, ab125212, Abcam) and detected using an Alexa Fluor 488-conjugated secondary antibody (Invitrogen). All sections were counterstained with DAPI (Invitrogen). Fluorescence images were acquired using an AxioObserver Z1 inverted microscope. A minimum of 7 slides were stained from a total of three hydrogels for each set of conditions.

Statistical analysis. Data were compared by using a two-way ANOVA test in GraphPad Prism software. Error bars represent the mean±standard deviation of measurements ($*p<0.05$, $p<0.01$, $*p<0.001$, and $****p<0.0001$).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A hydrogel precursor solution comprising a first polymer, a second polymer, Schwann cells, and a solvent, wherein the first polymer is methacrylated tropoelastin and the second polymer is methacrylated gelatin.

2. The solution of claim 1, wherein the solvent is distilled water or saline solution.

3. The solution of claim 1, having a total polymer concentration of between about 5% and about 25% (w/v).

4. The solution of claim 3, wherein the ratio of the first polymer to second polymer is between about 10/90 to about 90/10.

5. The solution of claim 1, wherein the methacrylated tropoelastin was prepared by methacrylation of human tropoelastin isoform SHELΔ26A.

6. The solution of claim 1, wherein the methacrylated gelatin was prepared by methacrylation of fish gelatin.

7. The solution of claim 1, further comprising a light activated photoinitiator in an amount suitable to form a hydrogel from the solution upon activation with UV and/or visible light.

8. The solution of claim 7, wherein the amount of the light activated photoinitiator is about 0.1% to about 1% (w/v).

9. The solution of claim 7, wherein the light activated photoinitiator is a UV or visible light activated photoinitiator.

10. The solution of claim 8, wherein the light activated photoinitiator is 2-hydroxy-4'-(2-hydroxyethoxy)-2-methylpropiophenone, Eosin Y (2-(2,4,5,7-tetrabromo-6-oxido-3-oxo-3H-xanthen-9-yl)benzoate), or lithium phenyl-2,4,6-trimethylbenzoylphospinate.

11. The solution of claim 1, wherein the solution contains the Schwann cells at a concentration of about $1 \times 10^6$ cells/ml to about $30 \times 10^6$ cells/ml.

12. A method for nerve repair in a subject, the method comprising (1) applying a hydrogel precursor solution to a location of nerve injury in the subject, the hydrogel precursor solution comprising a first polymer, a second polymer, Schwann cells, and a solvent, wherein the first polymer is methacrylated tropoelastin, and the second polymer is methacrylated gelatin; and (2) crosslinking the first polymer with the second polymer.

13. The method of claim 12, wherein the hydrogel precursor solution further comprises a light activated photoinitiator in an amount suitable to form a hydrogel from the solution upon activation with light, and crosslinking includes light activating the photoinitiator to form a hydrogel.

14. The method of claim 12, further comprising filling the lumen of nerve conduits in the location of nerve injury with the hydrogel precursor solution.

15. The method of claim 12, wherein the location of nerve injury is in a space between nerve ends in need of reconnecting, and applying the hydrogel precursor solution comprises filling the space between the nerve ends with the hydrogel precursor solution.

16. The method of claim 12, wherein more than one formulation ratio of first polymer and second polymer is utilized to form a core and shell nerve guidance conduit.

17. The method of claim 16, wherein the core is formed using the hydrogel precursor solution with a concentration of methacrylated gelatin which is higher than in the shell.

18. The method of claim 17, wherein the shell is formed using the hydrogel precursor solution with a concentration of methacrylated tropoelastin which is higher than in the core.

* * * * *